United States Patent [19]

Li et al.

[11] Patent Number: 5,087,777
[45] Date of Patent: Feb. 11, 1992

[54] PARTIALLY FLUORINATED ALKENES HAVING A TERTIARY STRUCTURE

[75] Inventors: Chien C. Li, East Aurora; Kane D. Cook, Buffalo; Rajat S. Basu, Williamsville, all of N.Y.

[73] Assignee: Allied-Signal Inc., Morris Township, Morris County, N.J.

[21] Appl. No.: 622,877

[22] Filed: Dec. 4, 1990

[51] Int. Cl.$^5$ .............................................. C07C 21/18
[52] U.S. Cl. ...................... 570/136; 134/42; 252/364; 570/134; 570/142; 570/155; 570/164; 570/172; 570/175
[58] Field of Search ........................................ 570/136

[56] References Cited

U.S. PATENT DOCUMENTS

| | | | |
|---|---|---|---|
| 2,981,763 | 4/1961 | Neill et al. | 260/653.8 |
| 3,047,640 | 7/1962 | Sweeney et al. | 260/655.4 |
| 4,326,068 | 4/1982 | Anello et al. | 549/89 |
| 4,367,349 | 1/1983 | Anello | 570/140 |
| 4,626,608 | 12/1986 | Scherer, Jr. et al. | 570/134 |
| 4,760,205 | 7/1988 | Probat et al. | 570/137 |
| 4,943,595 | 7/1990 | Scherer, Jr. et al. | 514/722 |

FOREIGN PATENT DOCUMENTS

| | | |
|---|---|---|
| 256447 | 7/1990 | Japan. |
| 902590 | 8/1962 | United Kingdom. |
| 90/09972 | 7/1990 | World Int. Prop. O.. |

OTHER PUBLICATIONS

W. Brunskill et al., "Anionic Oligomerisation of Hexafluoropropene: Fission of a Carbon-Carbon Bond by Fluoride Ion", (1970), Chem. Comm., pp. 1444-1446.

Fleming et al., "Addition of Free Radicals to Unsaturated Systems", J. C. S. Perkin I, pp. 574-577.

Dyatkin et al., "The Perfluoro-t-Butyl Anion in the Synthesis of Organofluorine Compounds", (1976), Rus. Chem. Rev., pp. 607-614.

Haszeldine et al., "Fluoro-Olefin Chemistry Etc.", (1979), pp. 565-569.

Pogorelyi et al., "The Hydrogen Bond and CH Acidity", (1984), Russ. Chem. Rev., pp. 1154-1167.

*Primary Examiner*—J. E. Evans
*Attorney, Agent, or Firm*—Melanie L. Brown; Jay P. Friedenson

[57] ABSTRACT

Novel partially fluorinated alkenes having the Formula:

$$R'-\underset{\underset{R}{|}}{\overset{\overset{R}{|}}{C}}-H$$

wherein each R is the same or different and is selected from the group consisting of $CF_3$, $CHF_2$, $CH_2F$, and $CH_3CF_2$, and R' is an alkenyl or fluoroalkenyl group having 1 to 6 carbon atoms have utility as solvents in a variety of industrial cleaning applications including cold cleaning, dry cleaning, and defluxing of printed circuit boards.

14 Claims, No Drawings

PARTIALLY FLUORINATED ALKENES HAVING A TERTIARY STRUCTURE

FIELD OF THE INVENTION

This invention relates to novel partially fluorinated alkenes having a tertiary structure and 4 to 9 carbon atoms. These compounds are useful in a variety of vapor degreasing, cold cleaning, and solvent cleaning applications including defluxing and dry cleaning.

BACKGROUND OF THE INVENTION

Cold cleaning is an application where numerous solvents are used. In most cold cleaning applications, the soiled part is either immersed in the fluid or wiped with rags or similar objects soaked in solvents and allowed to air dry.

In cold cleaning applications, the use of the aerosol packaging concept has long been found to be a convenient and cost effective means of dispensing solvents. Aerosol products utilize a propellant gas or mixture of Propellant gases, preferably in a liquified gas rather than a compressed gas state, to generate sufficient pressure to expel the active ingredients, i.e. product concentrates such as solvents, from the container upon opening of the aerosol valve. The propellants may be in direct contact with the solvent, as in most conventional aerosol systems, or may be isolated from the solvent, as in barrier-type aerosol systems.

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For soils which are difficult to remove, where elevated temperature is necessary to improve the cleaning action of the solvent, or for large volume assembly line operations where the cleaning of metal parts and assemblies must be done efficiently and quickly, the conventional operation of a vapor degreaser consists of immersing the Part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-described operations are well known in the art. For example, Sherliker et al. in U.S. Pat. No. 3,085,918 disclose such suitable vapor degreasers comprising a boiling sump, a clean sump, a water separator, and other ancillary equipment.

Chlorofluorocarbon solvents, such as trichlorotrifluoroethane, have attained widespread use in recent years as effective, nontoxic, and nonflammable agents useful in degreasing applications and other solvent cleaning applications. One isomer of trichlorotrifluoroethane is 1,1,2-trichloro-1,2,2-trifluoroethane (known in the art as CFC-113). CFC-113 has a boiling point of about 47° C. and has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like.

Another commonly used solvent is chloroform (known in the art as HCC-20) which has a boiling point of about 63° C. Perchloroethylene is a commonly used dry cleaning and vapor degreasing solvent which has a boiling point of about 121° C. These compounds are disadvantageous for use as solvents because they are toxic; also, chloroform causes liver damage when inhaled in excess.

Although chlorine is known to contribute to the solvency capability of a compound, fully halogenated chlorofluorocarbons and hydrochlorocarbons are suspected of causing environmental problems in connection with the earth's protective ozone layer. Thus, the art is seeking new compounds which do not contribute to environmental problems but yet provide the solvency properties of CFC-113. From an environmental standpoint, partially fluorinated alkenes are of interest because they are considered to be stratospherically safe substitutes for the currently used fully halogenated chlorofluorocarbons.

It is an object of this invention to provide novel partially fluorinated alkenes which are liquid at room temperature and which are useful as solvents for use in vapor degreasing, cold cleaning, and other solvent cleaning applications including defluxing applications and dry cleaning.

Another object of the invention is to provide novel environmentally acceptable solvents for use in the aforementioned applications.

Other objects and advantages of the invention will become apparent from the following description.

DETAILED DESCRIPTION OF THE INVENTION

We have found a novel class of alkenes which we believe have good solvency characteristics. The present novel compounds are of the Formula:

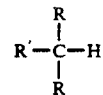

wherein each R is the same or different and is selected from the group consisting of $CF_3$, $CHF_2$, $CH_2F$, and $CH_3CF_2-$, and R' is an alkenyl or fluoroalkenyl group having 1 to 6 carbon atoms.

Because C in the Formula above has two alkyl groups and an alkenyl or fluoroalkenyl group thereon, these novel compounds have a tertiary structure. We believe that this tertiary structure provides good solvency power. When the present compounds are used as solvents, the compounds have good solvency power for polar contaminants such as polyols and amines and also for nonpolar contaminants including hydrocarbons such as mineral oil. We also believe that these novel compounds have boiling points which are comparable to those of currently used solvents.

Preferably, R' in the Formula above is selected from the group consisting of $CF_2=CF-$, $CF_2=CH-$, $CF_2=CFCF_2-$, $CF_2=CFCH_2-$, $CF_2=CFCHF-$, $CF_2=CHCF_2-$, $CF_2=CHCH_2-$, $CF_2=CHCHF-$, $CF_3CF=CF-$, $CF_3CF=CH-$, $CF_3CH=CF-$, $CF_3CH=CH-$, $CHF=CF-$, $CHF=CH-$, $CHF=CFCF_2-$, $CHF=CFCH_2-$, $CHF=CFCHF-$, $CHF=CHCF_2-$, $CHF=CHCH_2-$, $CHF=CHCHF-$, $CHF_2CF=CF-$, $CHF_2CF=CH-$, $CHF_2CH=CF-$, $CHF_2CH=CH-$, $CH_2=CF-$, $CH_2=CH-$, $CH_2=CFCF_2-$, $CH_2=CFCH_2-$, $CH_2=CFCHF-$, $CH_2=CHCF_2-$, $CH_2=CHCH_2-$, $CH_2=CHCHF-$, $CH_2FCF=CF-$, $CH_2FCF=CH-$, $CH_2FCH=CF-$, and $CH_2FCH=CH-$.

Also preferably, R' in the Formula above is selected from the group consisting of $CH_3CF=CF-$, $CH_3CF=CH-$, $CH_3CH=CF-$, $CH_3CH=CH-$, $CF_2=CFCF$ , $CF_2=CFCF_2CHF-$, $CF_2=CFCF$ $CF_2=CFCHFCF_2-$, $CF_2=CFCHFCHF-$, $CF_2=CFCHFCH_2-$, $CF_2=CFCH$ , $CF_2=CFCH_2CHF-$, $CF_2=CFCH$ $CF_2=CHCF$ $CF_2=CHCF_2CHF-$, $CF_2=CHCF$ , $CF_2=CHCHFCF_2-$, $CF_2=CHCHFCHF-$, $CF_2=CHCHFCH_2-$, $CF_2=CHCH$ $CF_2=CHCH_2CHF-$, $CF_2=CHCH$ $CHF=CFCF$ $CHF=CFCF_2CHF-$, $CHF=CFCF$ $CHF=CFCHFCF_2-$, $CHF=CFCHFCHF-$, $CHF=CFCHFCH_2-$, $CHF=CFCH$ $CHF=CFCH_2CHF-$, $CHF=CFCH$ $CHF=CHCF$ $CHF=CHCF_2CHF-$, $CHF=CHCF$ $CHF=CHCHFCF_2-$, $CHF=CHCHFCHF-$, $CHF=CHCHFCH_2-$, $CHF=CHCH$ $CHF=CHCH_2CHF-$, $CHF=CHCH$ $CH_2=CFCF$ $CH_2=CFCF_2CHF-$, $CH_2=CFCF$ $CH_2=CFCHFCF_2-$, $CH_2=CFCHFCHF-$, $CH_2=CFCHFCH_2-$, $CH_2=CFCH$ $CH_2=CFCH_2CHF-$, $CH_2=CFCH$ $CH_2=CHCF$ $CH_2=CHCF_2CHF-$, $CH_2=CHCF$ , $CH_2=CHCHFCF_2-$, $CH_2=CHCHFCHF-$, $CH_2=CHCHFCH_2-$, $CH_2=CHCH$ $CH_2=CHCH_2CHF-$, and $CH_2=CHCH$ Also preferably, R' in the Formula above is selected from the group consisting of $CF_3CF=CFCF_2-$, $CF_3CF=CFCHF-$, $CF_3CF=CFCH_2-$, $CHF_2CF=CFCF_2-$, $CHF_2CF=CFCHF-$, $CHF_2CF=CFCH_2-$, $CH_2FCF=CFCF_2-$, $CH_2FCF=CFCHF-$, $CH_2FCF=CFCH_2-$, $CH_3CF=CFCF_2-$, $CH_3CF=CFCHF-$, $CH_3CF=CFCH_2-$, $CF_3CF=CHCF_2-$, $CF_3CF=CHCHF-$, $CF_3CF=CHCH_2-$, $CHF_2CF=CHCF_2-$, $CHF_2CF=CHCHF-$, $CHF_2CFCHCH_2-$, $CH_2FCF=CHCF_2-$, $CH_2FCF=CHCHF-$, $CH_2FCF=CHCH_2-$, $CH_3CF=CHCF_2-$, $CH_3CF=CHCHF-$, $CH_3CF=CHCH_2-$, $CF_3CH=CFCF_2-$, $CF_3CH=CFCHF-$, $CF_3CH=CFCH_2-$, $CHF_2CH=CFCF_2-$, $CHF_2CH=CFCHF-$, $CHF_2CH=CFCH_2-$, $CH_2FCH=CFCF_2-$, $CH_2FCH=CFCHF-$, $CH_2FCH=CFCH_2-$, $CH_3CH=CFCF_2-$, $CH_3CH=CFCHF-$, $CH_3CH=CFCH_2-$, $CF_3CH=CHCF_2-$, $CF_3CH=CHCHF-$, $CF_3CH=CHCH_2-$, $CHF_2CH=CHCF_2-$, $CHF_2CH=CHCHF-$, $CHF_2CH=CHCH_2-$, $CH_2FCH=CHCF_2-$, $CH_2FCH=CHCHF-$, $CH_2FCH=CHCH_2-$, $CH_3CH=CHCF_2-$, $CH_3CH=CHCHF-$, and $CH_3CH=CHCH_2-$.

Also preferably, R' in the Formula above is selected from the group consisting of $CF_3CF_2CF=CF-$, $CF_3CH_2CF=CF-$, $CF_3CHFCF=CF-$, $CHF_2CHFCF=CF-$, $CHF_2CF_2CF=CF-$, $CHF_2CH_2CF=CF-$, $CH_2FF_2CF=CF-$, $CH_2FCHFCF=CF-$, $CH_2FCH_2CF=CF-$, $CH_3CF_2CF=CF-$, $CH_3CHFCF=CF-$, $CH_3$, $CH_2CF=CF-$, $CF_3CF_2CF=CH-$, $CF_3CHFCF=CH-$, $CF_3CH_2CF=CH-$, $CHF_2CF_2CF=CH-$, $CHF_2CHFCF=CH-$, $CHF_2CH_2CF=CH-$, $CH_2FF_2CF=CH-$, $CH_2FCHFCF=CH-$, $CH_2FCH_2CF=CH-$, $CH_3CF_2CF=CH-$, CH $CF_3CHFCF=CH-$, $CF_3CH_2CH=CF$ —, $CHF_2CF_2CH=CF-$, $CHF_2CHFCH=CF-$, $CH_2FF_2CH=CF-$, $CH_2FCH_2CH=CF-$, $CH_2FCHFCH=CF-$, $CH_3CF_2CH=CF-$, $CH_3CHFCH=CF-$, $CH_3CH_2CH=CF-$, $CF_3CF_2CH=CH-$, $CF_3CHFCH=CH-$, $CHF_2CF_2CH=CH-$, $CHF_2CH_2CH=CH-$, $CH_2FF_2CH=CH-$, $CH_2FCHFCH=CH-$, $CH_2FCH_2CH=CH-$, $CH_3CHFCH=CH-$, and $CH_3CH_2CH=CH-$.

In the Formula above, when one R is $CF_3$, the other R is $CHF_2$, and R' is $CF_2=CH-$, the compound is 2-fluoromethyl-1,1,1,4,4-pentafluoro-3-butene. When one R is $CF_3$, the other R is $CHF_2$, and R' is $CHF=CF-$, the compound is 2-fluoromethyl-1,1,1,3,4-pentafluoro-3-butene. When one R is $CF_3$, the other R is $CHF_2$, and R' is $CHF=CH-$, the compound is 2-fluoromethyl-1,1,1,4-tetrafluoro-3-butene.

Also in the Formula above, when one R is $CF_3$, the other R is $CHF_2$, and R' is $CH_2=CFCF_2-$, the compound is 4-difluoromethyl-2,3,3,5,5,5-hexafluoro-1-pentene. When one R is $CF_3$, the other R is $CHF_2$, and R' is $CH_3CF=CF-$, the compound 4-difluoromethyl-2,3,5,5,5-pentafluoro-1-pentene. When one R is $CF_3$, the other R is $CHF_2$, and R' is $CH_2=CHCF_2-$, the compound is 4-difluoromethyl-3,3,5,5,5-pentafluoro-1-Pentene. When one R is $CF_3$, the other R is $CHF_2$, and R' is $CH_3CH=CF-$, the compound is 4-difluoromethyl-3,5,5,5-tetrafluoro-1-pentene.

When one R is $CF_3$, the other R is $CH_2F$, and R' is $CH_2=CFCF_2-$, the compound is 4-fluoromethyl-2,3,3,5,5,5-hexafluoro-1-pentene. When one R is $CF_3$, the other R is $CH_2F$, and R' is $CH_3CF=CF-$, the compound is 4-fluoromethyl-2,3,5,5,5-pentafluoro-1-pentene. When one R is $CF_3$, the other R is $CH_2F$, and R' is $CH_2=CFCF_2-$, the compound is 4-fluoromethyl-3,3,5,5,5-pentafluoro-1-pentene. When one R is $CF_3$, the other R is $CH_2F$, and R' is $CH_3CH=CF-$, the compound is 4-fluoromethyl-3,5,5,5-tetrafluoro-1-pentene. When one R is $CF_3$, the other R is $CH_3CF_2-$, and R') is $CH_2=CF-$, the compound is 3-trifluoromethyl-2,4,4-trifluoro-1-pentene.

It is believed that the present novel compounds may be prepared by adapting known methods for preparing known alkenes coupled with the knowledge of one skilled in the art. For example, commercially available 3-chloropropionic acid may be fluorinated to form 1,1,1,3-tetrafluoropropane which may then be reacted with $CHF_2CF$ carbene to form 2-fluoromethyl-1,1,1,3,4,4-hexafluorobutane which may then be dehydrohalogenated to form 2-fluoromethyl-1,1,1,4,4-pentafluoro-3-butene.

As another example, commercially available 3-chloropropionic acid may be fluorinated to form 1,1,1,3-tetrafluoropropane which may then be reacted with $CHF_2CF$ carbene to form 2-fluoromethyl-1,1,1,3,4,4-hexafluorobutane which may then be dehydrohalogenated to form 2-fluoromethyl-1,1,1,3,4-pentafluoro-3-butene.

As another example, commercially available 3-chloropropionic acid may be fluorinated to form 1,1,1,3-tetrafluoropropane which may then be reacted with $CHF_2CF$ carbene to form 2-fluoromethyl-1,1,1,3,4,4-hexafluorobutane which may then be dehalogenated to form 2-fluoromethyl-1,1,1,4-tetrafluoro-3-butene.

As another example, 4-difluoromethyl-2,3,3,5,5,5-hexafluoro-1-pentene may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-pentene to form 2-trifluoromethyl-1,3,3,4,4-pentafluoropentane which may then be dehydrogenated to form 2-trifluoromethyl-1,3,3,4,4-pentafluoro-1-pentene. The 2-trifluoromethyl-1,3,3,4,4-pentafluoro-1-pentene may then be reacted with hydrogen fluoride to form 2-trifluoromethyl-1,1,3,3,4,4-hexafluoropentane which may then be dehydrohalogenated to form 4-difluoromethyl-2,3,3,5,5,5-hexafluoro-1-pentene.

As another example, 4-difluoromethyl-2,3,5,5,5-pentafluoro-1-pentene may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-Pentene to form 2-trifluoromethyl-1,3,3,4,4-pentafluoropentane which may then be dehydrogenated to form 2-trifluoromethyl-1,3,3,4,4-pentafluoro-1-pentene. The 2-trifluoromethyl-1,3,3,4,4-pentafluoro-1-pentene may then be reacted with hydrogen fluoride to form 2-trifluoromethyl-1,1,3,3,4,4-hexafluoropentane which may then be dehalogenated to form 4-difluoromethyl-2,3,5,5,5-pentafluoro-1-pentene.

As another example, 4-difluoromethyl-3,3,5,5,5-pentafluoro-1-pentene may be prepared by fluorinating 3-pentanone to form 3,3-difluoropentane which may then be dehydrogenated to form 3,3-difluoro-1-pentene. $CF_3$ may then be reacted with the 3,3-difluoro-1-pentene to form 2-trifluoromethyl-1,3,3-trifluoropentane which may then be dehydrogenated to form 2-trifluoromethyl-1,3,3-trifluoro-1-pentene. The 2-trifluoromethyl-1,3,3-trifluoro-1-pentene may then be reacted with hydrogen fluoride to form 2-trifluoromethyl-1,1,3,3-tetrafluoropentane which may then be dehydrohalogenated to form 4-difluoromethyl-3,5,5,5-tetrafluoro-1-pentene.

As another example, 4-fluoromethyl-2,3,3,5,5,5-hexafluoro-1-pentene may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-pentene to form 2-trifluoromethyl-1,3,3,4,4-pentafluoropentane which may then be dehydrohalogenated to form 4-fluoromethyl-2,3,3,5,5,5-hexafluoro-1-pentene.

As another example, 4-fluoromethyl-2,3,5,5,5-pentafluoro-1-pentene may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-pentene to form 2-trifluoromethyl-1,3,3,4,4-pentafluoropentane which may then be dehalogenated to form 4-fluoromethyl-2,3,5,5,5-pentafluoro-1-pentene.

As another example, 4-fluoromethyl-3,3,5,5,5-pentafluoro-1-pentene may be prepared by fluorinating 3-pentanone to form 3,3-difluoropentane which may then be dehydrogenated to form 3,3-difluoro-1-pentene. $CF_3$ may then be reacted with the 3,3-difluoro-1-pentene to form 2-trifluoromethyl-1,3,3-trifluoropentane which may then be dehydrogenated to form 4-fluoromethyl-3,3,5,5,5-pentafluoro-1-pentene.

As another example, 4-fluoromethyl-3,5,5,5-tetrafluoro-1-pentene may be prepared by fluorinating 3-pentanone to form 3,3-difluoropentane which may then be dehydrogenated to form 3,3-difluoro-1-pentene. $CF_3$ may then be reacted with the 3,3-difluoro-1-pentene to form 2-trifluoromethyl-1,3,3-trifluoropentane which may then be dehydrohalogenated to form 4-fluoromethyl-3,5,5,5-tetrafluoro-1-pentene.

As another example, commercially available 2,4-pentanedione may be fluorinated to form 2,2,4,4-tetrafluoropentane which may then be dehydrohalogenated to form 2,4,4-trifluoro-2-pentene. The 2,4,4-trifluoro-2-pentene may then be reacted with $CF_3$ to form 3-trifluoromethyl-2,2,4,4-tetrafluoropentane which may then be dehydrohalogenated to form 3-trifluoromethyl-2,4,4-trifluoro-1-pentene.

More preferably, each R in the formula above is $CF_3$. When R' is $CF_3CF=CH-$, the compound is 4-trifluoromethyl-1,1,1,2,5,5,5-heptafluoro-2-pentene.
When R' is $CF_2=CFCHF-$, the compound is 4-trifluoromethyl-1,1,2,3,5,5,5-heptafluoro-1-pentene.

As another example, commercially available hexafluoropropene may be oligomerized with commercially available trimethylamine in a dipolar aprotic solvent such as commercially available tetrahydrofuran to provide $(CF_3)_2C:CFCF_2CF_3$ as taught by W. Brunskill et al., "Anionic Oligomerisation of Hexafluoropropene: Fission of a Carbon-Carbon Bond by Fluoride Ion", *Chemical Communications,* 1444 (1970); the $(CF_3)_2C:CFCF_2CF_3$ may then be hydrogenated to form 2-trifluoromethyl-1,1,1,3,4,4,5,5,5-nonafluoropentane. The 2-trifluoromethyl-1,1,1,3,4,4,5,5,5-nonafluoropentane may then be dehalogenated to form 4-trifluoromethyl-1,1,1,2,5,5,5-heptafluoro-2-pentene.

As another example, commercially available hexafluoropropene may be oligomerized with commercially available trimethylamine in a dipolar aprotic solvent such as commercially available tetrahydrofuran to provide $(CF_3)_2C:CFCF_2CF_3$ as taught by W. Brunskill et al., "Anionic Oligomerisation of Hexafluoropropene: Fission of a Carbon-Carbon Bond by Fluoride Ion", *Chemical Communications,* 1444 (1970); the $(CF_3)_2C:CFCF_2CF_3$ may then be hydrogenated to form 2-trifluoromethyl-1,1,1,3,4,4,5,5,5-nonafluoropentane. The 2-trifluoromethyl-1,1,1,3,4,4,5,5,5-nonafluoropentane may then be dehalogenated to form 4-trifluoromethyl-1,1,2,3,5,5,5-heptafluoro-1-pentene.

Most Preferably, each R is $CF_3$ and R' is selected from the group consisting of $CF_2\!=\!CF\!-$, $CF_2\!=\!CH\!-$, $CHF\!=\!CH\!-$, $CH_2\!=\!CF\!-$, $CF_2\!=\!CFCF_2\!-$, $CF_3CF\!=\!CF\!-$, $CH_2\!=\!CFCF_2\!-$, $CH_3CF\!=\!CF\!-$, $CH_2\!=\!CHCF_2\!-$, and $CH_3CH\!=\!CF_2\!-$. The names of the preceding preferred hydrofluorocarbons are 3-trifluoromethyl-1,1,2,4,4,4-hexafluoro-1-butene; 3-trifluoromethyl-1,1,4,4,4-pentafluoro-1-butene; 3-trifluoromethyl-1,4,4,4-tetrafluoro-1-butene; 3-trifluoromethyl-2,4,4,4-tetrafluoro-1-butene; 4-trifluoromethyl-1,1,2,3,3,5,5,5-octafluoro-1-pentene; 4-trifluoromethyl-1,1,1,2,3,5,5,5-octafluoro-2-pentene; 4-trifluoromethyl-2,3,3,5,5,5-hexafluoro-1-pentene; 4-trifluoromethyl-2,3,5,5,5-pentafluoro-1-pentene; 4-trifluoromethyl-3,3,5,5,5-pentafluoro-1-pentene; and 4-trifluoromethyl-3,5,5,5-tetrafluoro-1-pentene.

As another example, 3-trifluoromethyl-1,1,2,4,4,4-hexafluoro-1-butene may be prepared by reacting commercially available 1,1-difluoroethylene according to the procedure of George L. Fleming et al., "Addition of Free Radicals to Unsaturated Systems. Part XX. The Direction of Radical Addition of Heptafluoro-2-iodopropane to Vinyl Fluoride, Trifluoroethylene, and Hexafluoropropene", *J.C.S. Perkin I*, 574 (1973) to form a product which may then be fluorinated to form 2-trifluoromethyl-1,1,1,2,3,4,4,4-octafluorobutane. The 2-trifluoromethyl-1,1,1,2,3,4,4,4-octafluorobutane may then be dehydrohalogenated and then hydrogenated to form 2-trifluoromethyl-1,1,1,3,4,4,4-heptafluorobutane. The 2-trifluoromethyl-1,1,1,3,4,4,4-heptafluorobutane may then be dehydrohalogenated to form 3-trifluoromethyl-1,1,2,4,4,4-hexafluoro-1-butene.

As another example, 3-trifluoromethyl-1,1,4,4,4-pentafluoro-1-butene may be prepared by reacting commercially available 1,1-difluoroethylene according to the procedure of George L. Fleming et al., supra, to form a product which may then be reacted With hydrogen fluoride to form 2-trifluoromethyl-1,1,1,2,4,4,4-hexafluorobutane which may then be dehydrohalogenated and then hydrogenated to form 2-trifluoromethyl-1,1,1,4,4,4-hexafluorobutane. The 2-trifluoromethyl-1,1,1,4,4,4-hexafluorobutane may then be dehydrohalogenated to form 3-trifluoromethyl-1,1,4,4,4-pentafluoro-1-butene.

As another example, 3-trifluoromethyl-1,4,4,4-tetrafluoro-1-butene may be prepared by reacting commercially available 1,1-difluoroethylene according to the procedure of George L. Fleming et al., supra, to form a product which may then be hydrogenated to form 2-trifluoromethyl-1,1,1,2,4,4-hexafluorobutane which may then be dehydrohalogenated and then hydrogenated to from 2-trifluoromethyl-1,1,1,4,4-pentafluorobutane. The 2-trifluoromethyl-1,1,1,4,4-pentafluorobutane may then be dehydrohalogenated to form 3-trifluoromethyl-1,4,4,4-tetrafluoro-1-butene.

As another example, 3-trifluoromethyl-2,4,4,4-tetrafluoro-1-butene may be prepared by fluorinating commercially available 2-butanone to form 2,2-difluorobutane which may then be dehydrogenated to form 3,3-difluoro-1-butene. $CF_3$ may then be added to the 3,3-difluoro-1-butene to form 2-trifluoromethyl-1,3,3-trifluorobutane which may then be dehydrogenated to form 2-trifluoromethyl-1,3,3-trifluoro-1-butene. The 2-trifluoromethyl-1,3,3-trifluoro-1-butene may then be reacted with hydrogen fluoride to for 2-difluoromethyl-1,1,1,3,3-pentafluorobutane which may then be dehydrogenated to form 2-trifluoromethyl-1,1,3,3-tetrafluoro-1-butene which may then be reacted with hydrogen fluoride to form 2-trifluoromethyl-1,1,1,1,3,3-pentafluorobutane. The 2-trifluoromethyl-1,1,1,3,3-pentafluorobutane may then be dehydrohalogenated to form 3-trifluoromethyl-2,4,4,4-tetrafluoro-1-butene.

As another example, commercially available hexafluoropropene may be oligomerized with commercially available trimethylamine in a dipolar aprotic solvent such as commercially available tetrahydrofuran to provide $(CF_3)_2C\!:\!CFCF_2CF_3$ which is then reacted with commercially available hydrogen fluoride to yield 2-trifluoromethyl-1,1,1,3,3,4,4,5,5,5-decafluoropentane as taught by W. Brunskill et al., "Anionic Oligomerisation of Hexafluoropropene: Fission of a Carbon-Carbon Bond by Fluoride Ion", *Chemical Communications*, 1444 (1970). The 2-trifluoromethyl-1,1,1,3,3,4,4,5,5,5-decafluoropentane may then be dehalogenated to form 4-trifluoromethyl-1,1,2,3,3,5,5,5-octafluoro-1-pentene.

As another example, commercially available hexafluoropropene may be oligomerized with commercially available trimethylamine in a dipolar aprotic solvent such as commercially available tetrahydrofuran to provide $(CF_3)_2C\!:\!CFCF_2CF_3$ which is then reacted with commercially available hydrogen fluoride to yield 2-trifluoromethyl-1,1,1,3,3,4,4,5,5,5-decafluoropentane as taught by W. Brunskill et al., "Anionic Oligomerisation of Hexafluoropropene: Fission of a Carbon-Carbon Bond by Fluoride Ion", *Chemical Communications*, 1444 (1970). The 2-trifluoromethyl-1,1,1,3,3,4,4,5,5,5-decafluoropentane may then be dehalogenated to form 4-trifluoromethyl-1,1,1,2,3,5,5,5-octafluoro-2-pentene.

As another example, 4-trifluoromethyl-2,3,3,5,5,5-hexafluoro-1-pentene may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-pentene to form 2-trifluoromethyl-1,3,3,4,4-pentafluoropentane which may then be dehydrogenated to form 2-trifluoromethyl-1,3,3,4,4-pentafluoro-1-pentene. The 2-trifluoromethyl-1,3,3,4,4-pentafluoro-1-pentene may then be reacted with hydrogen fluoride to form 2-trifluoromethyl-1,1,3,3,4,4-hexafluoropentane which may then be dehydrogenated to form 2-trifluoromethyl-1,1,3,3,4,4-hexafluoro-1-pentene which may then be reacted with hydrogen fluoride to form 2-trifluoromethyl-1,1,1,3,3,4,4-heptafluoropentane. The 2-trifluoromethyl-1,1,1,3,3,4,4-heptafluoropentane may then be dehydrohalogenated to form 4-trifluoromethyl-2,3,3,5,5,5-hexafluoro-1-pentene.

As another example, 4-trifluoromethyl-2,3,5,5,5-pentafluoro-1-pentene may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-pentene to form 2-trifluoromethyl-1,3,3,4,4-pentafluoropentane which may then be dehydrogenated to form 2-trifluoromethyl-1,3,3,4,4-pentafluoro-1-pentene. The 2-trifluoromethyl-1,3,3,4,4-pentafluoro-1-pentene may then be reacted with hydrogen fluoride to form 2-trifluoromethyl-1,1,3,3,4,4-hexafluoropentane which may then be dehydrogenated to form 2-trifluoromethyl-1,1,3,3,4,4-hexafluoro-1-pentene which may then be reacted with hydrogen fluoride to form 2-trifluoromethyl-1,1,1,3,3,4,4-heptafluoropentane. The 2- trifluoromethyl-1,1,1,3,3,4,4-heptafluoropentane may then be dehalogenated to form 4-trifluoromethyl-2,3,5,5,5-pentafluoro-1-pentene.

As another example, 4-trifluoromethyl-3,3,5,5,5-pentafluoro-1-pentene may be prepared by fluorinating 3-pentanone to form 3,3-difluoropentane which may then be dehydrogenated to form 3,3-difluoro-1-pentene. $CF_3$ may then be reacted with the 3,3-difluoro-1-pentene to form 2-trifluoromethyl-1,3,3-trifluoropentane which may then be dehydrogenated to form 2-trifluoromethyl-1,3,3-trifluoro-1-pentene. The 2-trifluoromethyl-1,3,3-trifluoro-1-pentene may then be reacted with hydrogen fluoride to form 2-trifluoromethyl-1,1,3,3-tetrafluoropentane which may then be dehydrogenated to form 2-trifluoromethyl-1,1,3,3-tetrafluoro-1-pentene which may then be reacted with hydrogen fluoride to form 2-trifluoromethyl-1,1,1,3,3-pentafluoropentane. The 2-trifluoromethyl-1,1,1,3,3-pentafluoropentane may then be dehydrogenated to form 4-trifluoromethyl-3,3,5,5,5-Pentafluoro-1-pentene.

As another example, 4-trifluoromethyl-3,5,5,5-tetrafluoro-1-pentene may be prepared by fluorinating 3-pentanone to form 3,3-difluoropentane which may then be dehydrogenated to form 3,3-difluoro-1-pentene. $CF_3$ may then be reacted with the 3,3-difluoro-1-pentene to form 2-trifluoromethyl-1,3,3-trifluoropentane which may then be dehydrogenated to form 2-trifluoromethyl-1,3,3-trifluoro-1-pentene. The 2-trifluoromethyl-1,3,3-trifluoro-1-pentene may then be reacted with hydrogen fluoride to form 2-trifluoromethyl-1,1,3,3-tetrafluoropentane which may then be dehydrogenated to form 2-trifluoromethyl-1,1,3,3-tetrafluoro-1-pentene which may then be reacted with hydrogen fluoride to form 2-trifluoromethyl-1,1,1,3,3-pentafluoropentane. The 2-trifluoromethyl-1,1,1,3,3-pentafluoropentane may then be dehydrohalogenated to form 4-trifluoromethyl-3,5,5,5-tetrafluoro-1-pentene.

The present compounds are useful as solvents for use in vapor degreasing and other solvent cleaning applications including defluxing, cold cleaning, dry cleaning, dewatering, decontamination, spot cleaning, aerosol propelled rework, extraction, particle removal, and surfactant cleaning applications. These compounds are also useful as blowing agents, Rankine cycle and absorption refrigerants, power fluids, and especially as refrigerants for centrifugal refrigeration chillers.

The present invention also provides a method of cleaning a solid surface which comprises treating the surface with a compound having the Formula:

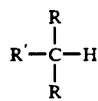

wherein each R is the same or different and is selected from the group consisting of $CF_3$, $CHF_2$, $CH_2F$, and $CH_3CF_2$, and R' is an alkenyl or fluoroalkenyl group having 1 to 6 carbon atoms.

Preferably, R' in the Formula above is selected from the group consisting of $CF_2=CF-$, $CF_2=CH-$, $CF_2=CFCF_2-$, $CF_2=CFCH_2-$, $CF_2=CFCHF-$, $CF_2=CHCF_2-$, $CF_2=CHCH_2-$, $CF_2=CHCHF-$, $CF_3CF=CF-$, $CF_3CF=CH-$, $CF_3CH=CF-$, $CF_3CH=CH-$, $CHF=CF-$, $CHF=CH-$, $CHF=CFCF_2-$, $CHF=CFCH_2-$, $CHF=CFCHF-$, $CHF=CHCF_2-$, $CHF=CHCH_2-$, $CHF=CHCHF-$, $CHF_2CF=CF-$, $CHF_2CF=CH-$, $CHF_2CH=CF-$, $CHF CH=CH-$, $CH_2=CF-$, $CH_2=CH-$, $CH_2=CFCF_2-$, $CH_2=CFCH_2-$, $CH_2=CFCHF-$, $CH_2=CHCF_2-$, $CH_2=CHCH_2-$, $CH_2=CHCHF-$, $CH_2FCF=CF-$, $CH_2FCF=CH-$, $CH_2FCH=CF-$, and $CH_2FCH=CH-$.

Also preferably, R' in the Formula above is selected from the group consisting of $CH_3CF=CF-$, $CH_3CF=CH-$, $CH_3CH=CF-$, $CH_3CH=CH-$, $CF_2=CFCF$ $CF_2=CFCF_2CHF-$, $CF_2=CFCF$ , $CF_2=CFCHFCF_2-$, $CF_2=CFCHFCHF-$, $CF_2=CFCHFCH_2-$, $CF_2=CFCH$ , $CF_2=CFCH_2CHF-$, $CF_2=CFCH_2CH_2$, $CF_2=CHCF_2CF_2-$, $CF_2=CHCF_2CHF-$, $CF_2=CHCF$ $CF_2=CHCHFCF_2-$, $CF_2=CHCHFCHF-$, $CF_2=CHCHFCH_2-$, $CF_2=CHCH_2CF_2-$, $CF_2=CHCH_2CHF-$, $CF_2=CHCH$ $CHF=CFCF_2CF_2-$, $CHF=CFCF_2CHF-$, $CHF=CFCF$ $CHF=CFCHFCF_2-$, $CHF=CFCHFCHF-$, $CHF=CFCHFCH_2-$, $CHF=CFCH_2CF_2-$, $CHF=CFCH_2CHF-$, $CHF=CFCH_2CH_2-$, $CHF=CHCF_2CF_2-$, $CHF=CHCF_2CHF-$, $CHF=CHCF_2CH_2-$, $CHF=CHCHFCF_2-$, $CHF=CHCHFCHF-$, $CHF=CHCHFCH_2-$, $CHF=CHCH_2CF_2-$, $CHF=CHCH_2CHF-$, $CHF=CHCH_2CH_2-$, $CH_2=CFCF_2CF_2-$, $CH_2=CFCF_2CHF-$, $CH_2=CFCF_2CH_2-$, $CH_2=CFCHFCF_2-$, $CH_2=CFCHFCHF-$, $CH_2=CFCHFCH_2-$, $CH_2=CFCH_2CF_2-$, $CH_2=CFCH_2CHF-$, $CH_2=CHCF_2CH_2-$, $CH_2=CHCF_2CF_2-$, $CH_2=CHCF_2CHF-$, $CH_2=CHCF_2CH_2-$, $CH_2=CHCHFCF_2-$, $CH_2=CHCHFCHF-$, $CH_2=CHCHFCH_2-$, $CH_2=CHCH$ $CH_2=CHCH_2CHF-$, and $CH_2=CHCH_2CH_2-$.

Also preferably, R' in the Formula above is selected from the group consisting of $CF_3CF=CF=CFCF_2-$, $CF_3CF=CFCHF-$, $CF_3CF=CFCH_2-$, $CHF_2CF=CFCF_2-$, $CHF_2CF=CFCHF-$, $CHF_2CF=CFCH_2-$, $CH_2FCF=CFCF_2-$, $CH_2FCF=CFCHF-$, $CH_2FCF=CFCH_2-$, $CH_3CF=CFCF_2-$, $CH_3CF=CFCHF-$, $CH_3CF=CFCH_2-$, $CF_3CF=CHCF_2-$, $CF_3CF=CHCHF-$, $CF_3CF=CHCH_2-$, $CHF_2CF=CHCF_2-$, $CHF_2CF=CHCHF-$, $CHF_2CF=CHCH_2-$, $CH_2FCF=CHCF_2-$, $CH_2FCF=CHCHF-$, $CH_2FCF=CHCH_2-$, $CH_3CF=CHCF_2-$, $CH_3CF=CHCHF-$, $CH_3CF=CHCH_2-$, $CF_3CH=CFCF_2-$, $CF_3CH=CFCHF-$, $CF_3CH=CFCH_2-$, $CHF_2CH=CFCF_2-$, $CHF_2CH=CFCHF-$, $CHF_2CH=CFCH_2-$, $CH_2FCH=CFCF_2-$, $CH_2FCH=CFCHF-$, $CH_2FCH=CFCH_2-$, $CH_3CH=CFCF_2-$, $CH_3CH=CFCHF-$, $CH_3CH=CFCH_2-$, $CF_3CH=CHCF_2-$, $CF_3CH=CHCHF-$, $CF_3CH=CHCH_2-$, $CHF_2CH=CHCF_2-$, $CHF_2CH=CHCHF-$, $CHF_2CH=CHCH_2-$, $CH_2FCH=CHCF_2-$, $CH_2FCH=CHCHF-$, $CH_2FCH=CHCH_2-$, $CH_3CH=CHCF_2-$, $CH_3CH=CHCHF-$, and $CH_3CH=CHCH_2-$.

Also preferably, R' in the Formula above is selected from the group consisting of $CF_3CF_2CF=CF-$, $CF_3CHFCF=CF-$, $CF_3CH_2CF=CF-$, $CHF_2CF_2=CF-$, $CHF_2CHFCF=CHFCF=CF-$, $CHF_2CH_2CF=CF-$, $CH_2FF_2CF=CF-$, $CH_2FCHFCF=CF-$, $CH_2FCH_2CF=CF-$,
$CH_3CF_2CF=CF-$, $CH_3CHFCF=CF-$,
$CH_3CH_2CF=CF-$, $CF_3CF_2CRF=CH-$,
$CF_3CHFCF=CH-$, $CF_3CH_2CF=C-$,
$CHF_2CF_2CF=CH-$, $CHF_2CHFCF=CH-$,
$CHF_2CH_2CF=CH-$, $CH_2FF_2CF=CH-$,
$CH_2FCHFCF=CH-$, $CH_2FCH_2CF=CH-$,
$CH_3CF_2CF=CH-$, $CH_3CHFCF=CH-$,
$CH_3CH_2CF=CH-$, $CF_3CF_2CH=CF-$,
$CF_3CHFCH=CF-$, $CF_3CH_2CH=CF-$,
$CHF_2CF_2CH=CF-$, $CHF_2CHFCH=CF-$,
$CHF_2CH_2CH=CF-$, $CH_2FF_2CH=CF-$,
$CH_2FCHFCH=CF-$, $CH_2FCH_2CH=CF-$,
$CH_3CF_2CH=CF-$, $CH_3CHFCH=CF-$,
$CH_3CH_2CH=CF-$, $CF_3CF_2CH=CH-$,
$CF_3CHFCH=CH-$, $CF_3CH_2CH=CH-$,
$CHF_2CF_2CH=CH-$, $CHF_2CHFCH=CH-$,
$CHF_2CH_2CH=CH-$, $CH_2FF_2CH=CH-$,
$CH_2FCHFCH=CH-$, $CH_2FCH_2CH=CH-$,
$CH_3CF_2CH=CH-$, $CH_3CHFCH=CH-$, and
$CH_3CH_2CH=CH-$.

In the Process embodiment of the invention, the compositions may be used to clean solid surfaces by treating the surfaces with the compounds in any manner well known to the art such as by dipping or spraying or use of conventional degreasing apparatus.

When the novel compounds are used to clean solid surfaces by spraying the surfaces with the compounds, preferably, the novel compounds are sprayed onto the surfaces by using a propellant. Preferably, the propellant is selected from the group consisting of hydrochlorofluorocarbon, hydrofluorocarbon, and mixtures thereof. Useful hydrochlorofluorocarbon propellants include dichlorofluoromethane (known in the art as HCFC-21), chlorodifluoromethane (known in the art as HCFC-22), 1,1-dichloro-2,2-difluoroethane (known in the art as HCFC-132a), 1-chloro-2,2,2-trifluoroethane (known in the art as HCFC-133), and 1-chloro-1,1-difluoroethane (known in the art as HCFC-142b); commercially available HCFC-21, HCFC-22, and HCFC-142b may be used in the present invention. Useful hydrofluorocarbon propellants include trifluoromethane (known in the art as HFC-23), 1,1,1,2-tetrafluoroethane (known in the art as HFC-134a), and 1,1-difluoroethane (known in the art as HFC-152a); commercially available HFC-23 and HFC-152a may be used in the present invention. Until HFC-134a becomes available in commercial quantities, HFC-134a may be made by a known method such as that disclosed by U.S. Pat. No. 4,851,595. Preferred propellants include chlorodifluoromethane and 1,1,1,2-tetrafluoroethane.

The present invention is more fully illustrated by the following non-limiting Examples.

EXAMPLES 1-960

For each example, the novel compound of the Formula above having the R and R' groups as indicated in Table I below is made.

TABLE I

| Example | R | R' |
|---|---|---|
| 1 | $CF_3$, $CHF_2$ | $CF_2=CF-$ |
| 2 | $CF_3$, $CHF_2$ | $CF_2=CH-$ |
| 3 | $CF_3$, $CHF_2$ | $CF_2=CFCF_2-$ |
| 4 | $CF_3$, $CHF_2$ | $CF_2=CFCH_2-$ |
| 5 | $CF_3$, $CHF_2$ | $CF_2=CFCHF-$ |
| 6 | $CF_3$, $CHF_2$ | $CF_2=CHCF_2-$ |
| 7 | $CF_3$, $CHF_2$ | $CF_2=CHCH_2-$ |
| 8 | $CF_3$, $CHF_2$ | $CF_2=CHCHF-$ |

TABLE I-continued

| Example | R | R' |
|---|---|---|
| 9 | $CF_3$, $CHF_2$ | $CF_3CF=CF-$ |
| 10 | $CF_3$, $CHF_2$ | $CF_3CF=CH-$ |
| 11 | $CF_3$, $CHF_2$ | $CF_3CH=CF-$ |
| 12 | $CF_3$, $CHF_2$ | $CF_3CH=CH-$ |
| 13 | $CF_3$, $CHF_2$ | $CHF=CF-$ |
| 14 | $CF_3$, $CHF_2$ | $CHF=CH-$ |
| 15 | $CF_3$, $CHF_2$ | $CHF=CFCF_2-$ |
| 16 | $CF_3$, $CHF_2$ | $CHF=CFCH_2-$ |
| 17 | $CF_3$, $CHF_2$ | $CHF=CFCHF-$ |
| 18 | $CF_3$, $CHF_2$ | $CHF=CHCF_2-$ |
| 19 | $CF_3$, $CHF_2$ | $CHF=CHCH_2-$ |
| 20 | $CF_3$, $CHF_2$ | $CHF=CHCHF-$ |
| 21 | $CF_3$, $CHF_2$ | $CHF_2CF=CF-$ |
| 22 | $CF_3$, $CHF_2$ | $CHF_2CF=CH-$ |
| 23 | $CF_3$, $CHF_2$ | $CHF_2CH=CF-$ |
| 24 | $CF_3$, $CHF_2$ | $CHF_2CH=CH-$ |
| 25 | $CF_3$, $CHF_2$ | $CH_2=CF-$ |
| 26 | $CF_3$, $CHF_2$ | $CH_2=CH-$ |
| 27 | $CF_3$, $CHF_2$ | $CH_2=CFCF_2-$ |
| 28 | $CF_3$, $CHF_2$ | $CH_2=CFCH_2-$ |
| 29 | $CF_3$, $CHF_2$ | $CH_2=CFCHF-$ |
| 30 | $CF_3$, $CHF_2$ | $CH_2=CHCF_2-$ |
| 31 | $CF_3$, $CHF_2$ | $CH_2=CHCH_2-$ |
| 32 | $CF_3$, $CHF_2$ | $CH_2=CHCHF-$ |
| 33 | $CF_3$, $CHF_2$ | $CH_2FCF=CF-$ |
| 34 | $CF_3$, $CHF_2$ | $CH_2FCF=CH-$ |
| 35 | $CF_3$, $CHF_2$ | $CH_2FCH=CF-$ |
| 36 | $CF_3$, $CHF_2$ | $CH_2FCH=CH-$ |
| 37 | $CF_3$, $CHF_2$ | $CH_3CF=CF-$ |
| 38 | $CF_3$, $CHF_2$ | $CH_3CF=CH-$ |
| 39 | $CF_3$, $CHF_2$ | $CH_3CH=CF-$ |
| 40 | $CF_3$, $CHF_2$ | $CH_3CH=CH-$ |
| 41 | $CF_3$, $CHF_2$ | $CF_2=CFCF_2CF_2-$ |
| 42 | $CF_3$, $CHF_2$ | $CF_2=CFCF_2CHF-$ |
| 43 | $CF_3$, $CHF_2$ | $CF_2=CFCF_2CH_2-$ |
| 44 | $CF_3$, $CHF_2$ | $CF_2=CFHFCF_2-$ |
| 45 | $CF_3$, $CHF_2$ | $CF_2=CFCHFCHF-$ |
| 46 | $CF_3$, $CHF_2$ | $CF_2=CFCHFCH_2-$ |
| 47 | $CF_3$, $CHF_2$ | $CF_2=CFCH_2CF_2-$ |
| 48 | $CF_3$, $CHF_2$ | $CF_2=CFCH_2CHF-$ |
| 49 | $CF_3$, $CHF_2$ | $CF_2=CFCH_2CH_2-$ |
| 50 | $CF_3$, $CHF_2$ | $CF_2=CHCF_2CF_2-$ |
| 51 | $CF_3$, $CHF_2$ | $CF_2=CHCF_2CHF-$ |
| 52 | $CF_3$, $CHF_2$ | $CF_2=CHCF_2CH_2-$ |
| 53 | $CF_3$, $CHF_2$ | $CF_2=CHCHFCF_2-$ |
| 54 | $CF_3$, $CHF_2$ | $CF_2=CHCHFCHF-$ |
| 55 | $CF_3$, $CHF_2$ | $CF_2=CHCHFCH_2-$ |
| 56 | $CF_3$, $CHF_2$ | $CF_2=CHCH_2CF_2-$ |
| 57 | $CF_3$, $CHF_2$ | $CF_2=CHCH_2CHF-$ |
| 58 | $CF_3$, $CHF_2$ | $CF_2=CHCH_2CH_2-$ |
| 59 | $CF_3$, $CHF_2$ | $CHF=CFCF_2CF_2-$ |
| 60 | $CF_3$, $CHF_2$ | $CHF=CFCF_2CHF-$ |
| 61 | $CF_3$, $CHF_2$ | $CHF=CFCF_2CH_2-$ |
| 62 | $CF_3$, $CHF_2$ | $CHF=CFCHFCF_2-$ |
| 63 | $CF_3$, $CHF_2$ | $CHF=CFCHFCHF-$ |
| 64 | $CF_3$, $CHF_2$ | $CHF=CFCHFCH_2-$ |
| 65 | $CF_3$, $CHF_2$ | $CHF=CFCH_2CF_2-$ |
| 66 | $CF_3$, $CHF_2$ | $CHF=CFCH_2CHF-$ |
| 67 | $CF_3$, $CHF_2$ | $CHF=CFCH_2CH_2-$ |
| 68 | $CF_3$, $CHF_2$ | $CHF=CHCF_2CF_2-$ |
| 69 | $CF_3$, $CHF_2$ | $CHF=CHCF_2CHF-$ |
| 70 | $CF_3$, $CHF_2$ | $CHF=CHCF_2CH_2-$ |
| 71 | $CF_3$, $CHF_2$ | $CHF=CHCHFCF_2-$ |
| 72 | $CF_3$, $CHF_2$ | $CHF=CHCHFCHF-$ |
| 73 | $CF_3$, $CHF_2$ | $CHF=CHCHFCH_2-$ |
| 74 | $CF_3$, $CHF_2$ | $CHF=CHCH_2CF_2-$ |
| 75 | $CF_3$, $CHF_2$ | $CHF=CHCH_2CHF-$ |
| 76 | $CF_3$, $CHF_2$ | $CHF=CHCH_2CH_2-$ |
| 77 | $CF_3$, $CHF_2$ | $CH_2=CFCF_2CF_2-$ |
| 78 | $CF_3$, $CHF_2$ | $CH_2=CFCF_2CHF-$ |
| 79 | $CF_3$, $CHF_2$ | $CH_2=CFCF_2CH_2-$ |
| 80 | $CF_3$, $CHF_2$ | $CH_2=CFCHFCF_2-$ |
| 81 | $CF_3$, $CHF_2$ | $CH_2=CFCHFCHF-$ |
| 82 | $CF_3$, $CHF_2$ | $CH_2=CFCHFCH_2$ |
| 83 | $CF_3$, $CHF_2$ | $CH_2=CFCH_2CF_2-$ |
| 84 | $CF_3$, $CHF_2$ | $CH_2=CFCH_2CHF-$ |
| 85 | $CF_3$, $CHF_2$ | $CH_2=CFCH_2CH_2-$ |
| 86 | $CF_3$, $CHF_2$ | $CH_2=CHCF_2CF_2-$ |
| 87 | $CF_3$, $CHF_2$ | $CH_2=CHCF_2CHF-$ |
| 88 | $CF_3$, $CHF_2$ | $CH_2=CHCF_2CH_2-$ |
| 89 | $CF_3$, $CHF_2$ | $CH_2=CHCHFCF_2-$ |

TABLE I-continued

| Example | R | R' |
|---|---|---|
| 90 | CF$_3$, CHF$_2$ | CH$_2$=CHCHFCHF— |
| 91 | CF$_3$, CHF$_2$ | CH$_2$=CHCHFCH$_2$— |
| 92 | CF$_3$, CHF$_2$ | CH$_2$=CHCH$_2$CF$_2$— |
| 93 | CF$_3$, CHF$_2$ | CH$_2$=CHCH$_2$CHF— |
| 94 | CF$_3$, CHF$_2$ | CH$_2$=CHCH$_2$CH$_2$— |
| 95 | CF$_3$, CHF$_2$ | CF$_3$CF=CFCF$_2$— |
| 96 | CF$_3$, CHF$_2$ | CF$_3$CF=CFCHF— |
| 97 | CF$_3$, CHF$_2$ | CF$_3$CF=CFCF$_2$— |
| 98 | CF$_3$, CHF$_2$ | CF$_3$CF=CFCHF— |
| 99 | CF$_3$, CHF$_2$ | CF$_3$CF=CFCH$_2$— |
| 100 | CF$_3$, CHF$_2$ | CHF$_2$CF=CFCF$_2$— |
| 101 | CF$_3$, CHF$_2$ | CHF$_2$CF=CFCHF— |
| 102 | CF$_3$, CHF$_2$ | CHF$_2$CF=CFCH$_2$— |
| 103 | CF$_3$, CHF$_2$ | CH$_2$FCF=CFCF$_2$— |
| 104 | CF$_3$, CHF$_2$ | CH$_2$FCF=CFCHF— |
| 105 | CF$_3$, CHF$_2$ | CH$_2$FCF=CFCH$_2$— |
| 106 | CF$_3$, CHF$_2$ | CH$_3$CF=CFCF$_2$— |
| 107 | CF$_3$, CHF$_2$ | CH$_3$CF=CFCHF— |
| 108 | CF$_3$, CHF$_2$ | CH$_3$CF=CFCH$_2$— |
| 109 | CF$_3$, CHF$_2$ | CF$_3$CF=CHCF$_2$— |
| 110 | CF$_3$, CHF$_2$ | CF$_3$CF=CHCHF— |
| 111 | CF$_3$, CHF$_2$ | CF$_3$CF=CHCH$_2$— |
| 112 | CF$_3$, CHF$_2$ | CHF$_2$CF=CHCF$_2$— |
| 113 | CF$_3$, CHF$_2$ | CHF$_2$CF=CHCHF— |
| 114 | CF$_3$, CHF$_2$ | CHF$_2$CF=CHCH$_2$— |
| 115 | CF$_3$, CHF$_2$ | CH$_2$FCF=CHCF$_2$— |
| 116 | CF$_3$, CHF$_2$ | CH$_2$FCF=CHCHF— |
| 117 | CF$_3$, CHF$_2$ | CH$_2$FCF=CHCH$_2$— |
| 118 | CF$_3$, CHF$_2$ | CH$_3$CF=CHCF$_2$— |
| 119 | CF$_3$, CHF$_2$ | CH$_3$CF=CHCHF— |
| 120 | CF$_3$, CHF$_2$ | CH$_3$CF=CHCH$_2$— |
| 121 | CF$_3$, CHF$_2$ | CF$_3$CH=CFCF$_2$— |
| 122 | CF$_3$, CHF$_2$ | CF$_3$CH=CFCHF— |
| 123 | CF$_3$, CHF$_2$ | CF$_3$CH=CFCH$_2$— |
| 124 | CF$_3$, CHF$_2$ | CHF$_2$CH=CFCF$_2$— |
| 125 | CF$_3$, CHF$_2$ | CHF$_2$CH=CFCHF— |
| 126 | CF$_3$, CHF$_2$ | CHF$_2$CH=CFCH$_2$— |
| 127 | CF$_3$, CHF$_2$ | CH$_2$FCH=CFCF$_2$— |
| 128 | CF$_3$, CHF$_2$ | CH$_2$FCH=CFCHF— |
| 129 | CF$_3$, CHF$_2$ | CH$_2$FCH=CFCH$_2$— |
| 130 | CF$_3$, CHF$_2$ | CH$_3$CH=CFCF$_2$— |
| 131 | CF$_3$, CHF$_2$ | CH$_3$CH=CFCHF— |
| 132 | CF$_3$, CHF$_2$ | CH$_3$CH=CFCH$_2$— |
| 133 | CF$_3$, CHF$_2$ | CF$_3$CH=CHCF$_2$— |
| 134 | CF$_3$, CHF$_2$ | CF$_3$CH=CHCHF— |
| 135 | CF$_3$, CHF$_2$ | CF$_3$CH=CHCH$_2$— |
| 136 | CF$_3$, CHF$_2$ | CHF$_2$CH=CHCF$_2$— |
| 137 | CF$_3$, CHF$_2$ | CHF$_2$CH=CHCHF— |
| 138 | CF$_3$, CHF$_2$ | CHF$_2$CH=CHCH$_2$— |
| 139 | CF$_3$, CHF$_2$ | CH$_2$FCH=CHCF$_2$— |
| 140 | CF$_3$, CHF$_2$ | CH$_2$FCH=CHCHF— |
| 141 | CF$_3$, CHF$_2$ | CH$_2$FCH=CHCH$_2$— |
| 142 | CF$_3$, CHF$_2$ | CH$_3$CH=CHCF$_2$— |
| 143 | CF$_3$, CHF$_2$ | CH$_3$CH=CHCHF— |
| 144 | CF$_3$, CHF$_2$ | CH$_3$CH=CHCH$_2$— |
| 145 | CF$_3$, CHF$_2$ | CF$_3$CF$_2$CF=CF— |
| 146 | CF$_3$, CHF$_2$ | CF$_3$CHFCF=CF— |
| 147 | CF$_3$, CHF$_2$ | CF$_3$CH$_2$CF=CF— |
| 148 | CF$_3$, CHF$_2$ | CHF$_2$CF$_2$CF=CF— |
| 149 | CF$_3$, CHF$_2$ | CHF$_2$CHFCF=CF— |
| 150 | CF$_3$, CHF$_2$ | CHF$_2$CH$_2$CF=CF— |
| 151 | CF$_3$, CHF$_2$ | CH$_2$FF$_2$CF=CF— |
| 152 | CF$_3$, CHF$_2$ | CH$_2$FCHFCF=CF— |
| 153 | CF$_3$, CHF$_2$ | CH$_2$FCH$_2$CF=CF— |
| 154 | CF$_3$, CHF$_2$ | CH$_3$CF$_2$CF=CF— |
| 155 | CF$_3$, CHF$_2$ | CH$_3$CHFCF=CF— |
| 156 | CF$_3$, CHF$_2$ | CH$_3$CH$_2$CF=CF— |
| 157 | CF$_3$, CHF$_2$ | CF$_3$CF$_2$CF=CH— |
| 158 | CF$_3$, CHF$_2$ | CF$_3$CHFCF=CH— |
| 159 | CF$_3$, CHF$_2$ | CF$_3$CH$_2$CF=CH— |
| 160 | CF$_3$, CHF$_2$ | CHF$_2$CF$_2$CF=CH— |
| 161 | CF$_3$, CHF$_2$ | CHF$_2$CHFCF=CH— |
| 162 | CF$_3$, CHF$_2$ | CHF$_2$CH$_2$CF=CH— |
| 163 | CF$_3$, CHF$_2$ | CH$_2$FF$_2$CF=CH— |
| 164 | CF$_3$, CHF$_2$ | CH$_2$FCHFCF=CH— |
| 165 | CF$_3$, CHF$_2$ | CH$_2$FCH$_2$CF=CH— |
| 166 | CF$_3$, CHF$_2$ | CH$_3$CF$_2$CF=CH— |
| 167 | CF$_3$, CHF$_2$ | CH$_3$CHFCF=CH— |
| 168 | CF$_3$, CHF$_2$ | CH$_3$CH$_2$CF=CH— |
| 169 | CF$_3$, CHF$_2$ | CF$_3$CF$_2$CH=CF— |
| 170 | CF$_3$, CHF$_2$ | CF$_3$CHFCH=CF— |
| 171 | CF$_3$, CHF$_2$ | CF$_3$CH$_2$CH=CF— |
| 172 | CF$_3$, CHF$_2$ | CHF$_2$CF$_2$CH=CF— |
| 173 | CF$_3$, CHF$_2$ | CHF$_2$CHFCH=CF— |
| 174 | CF$_3$, CHF$_2$ | CHF$_2$CH$_2$CH=CF— |
| 175 | CF$_3$, CHF$_2$ | CH$_2$FF$_2$CH=CF— |
| 176 | CF$_3$, CHF$_2$ | CH$_2$FCHFCH=CF— |
| 177 | CF$_3$, CHF$_2$ | CH$_2$FCH$_2$CH=CF— |
| 178 | CF$_3$, CHF$_2$ | CH$_3$CF$_2$CH=CF— |
| 179 | CF$_3$, CHF$_2$ | CH$_3$CHFCH=CF— |
| 180 | CF$_3$, CHF$_2$ | CH$_3$CH$_2$CH=CF— |
| 181 | CF$_3$, CHF$_2$ | CF$_3$CF$_2$CH=CH— |
| 182 | CF$_3$, CHF$_2$ | CF$_3$CHFCH=CH— |
| 183 | CF$_3$, CHF$_2$ | CF$_3$CH$_2$CH=CH— |
| 184 | CF$_3$, CHF$_2$ | CHF$_2$CF$_2$CH=CH— |
| 185 | CF$_3$, CHF$_2$ | CHF$_2$CHFCH=CH— |
| 186 | CF$_3$, CHF$_2$ | CHF$_2$CH$_2$CH=CH— |
| 187 | CF$_3$, CHF$_2$ | CH$_2$FF$_2$CH=CH— |
| 188 | CF$_3$, CHF$_2$ | CH$_2$FCHFCH=CH— |
| 189 | CF$_3$, CHF$_2$ | CH$_2$FCH$_2$CH=CH— |
| 190 | CF$_3$, CHF$_2$ | CH$_3$CF$_2$CH=CH— |
| 191 | CF$_3$, CHF$_2$ | CH$_3$CHFCH=CH— |
| 192 | CF$_3$, CHF$_2$ | CH$_3$CH$_2$CH=CH— |
| 193 | CF$_3$, CH$_2$F | CF$_2$=CF— |
| 194 | CF$_3$, CH$_2$F | CF$_2$=CH— |
| 195 | CF$_3$, CH$_2$F | CF$_2$=CFCF$_2$— |
| 196 | CF$_3$, CH$_2$F | CF$_2$=CFCH$_2$— |
| 197 | CF$_3$, CH$_2$F | CF$_2$=CFCHF— |
| 198 | CF$_3$, CH$_2$F | CF$_2$=CHCF$_2$— |
| 199 | CF$_3$, CH$_2$F | CF$_2$=CHCH$_2$— |
| 200 | CF$_3$, CH$_2$F | CF$_2$=CHCHF— |
| 201 | CF$_3$, CH$_2$F | CF$_3$CF=CF— |
| 202 | CF$_3$, CH$_2$F | CF$_3$CF=CH— |
| 203 | CF$_3$, CH$_2$F | CF$_3$CH=CF— |
| 204 | CF$_3$, CH$_2$F | CF$_3$CH=CH— |
| 205 | CF$_3$, CH$_2$F | CHF=CF— |
| 206 | CF$_3$, CH$_2$F | CHF=CH— |
| 207 | CF$_3$, CH$_2$F | CHF=CFCF$_2$— |
| 208 | CF$_3$, CH$_2$F | CHF=CFCH$_2$— |
| 209 | CF$_3$, CH$_2$F | CHF=CFCHF— |
| 210 | CF$_3$, CH$_2$F | CHF=CHCF$_2$— |
| 211 | CF$_3$, CH$_2$F | CHF=CHCH$_2$— |
| 212 | CF$_3$, CH$_2$F | CHF=CHCHF— |
| 213 | CF$_3$, CH$_2$F | CHF$_2$CF=CF— |
| 214 | CF$_3$, CH$_2$F | CHF$_2$CF=CH— |
| 215 | CF$_3$, CH$_2$F | CHF$_2$CH=CF— |
| 216 | CF$_3$, CH$_2$F | CHF$_2$CH=CH— |
| 217 | CF$_3$, CH$_2$F | CH$_2$=CF— |
| 218 | CF$_3$, CH$_2$F | CH$_2$=CH— |
| 219 | CF$_3$, CH$_2$F | CH$_2$=CFCF$_2$— |
| 220 | CF$_3$, CH$_2$F | CH$_2$=CFCH$_2$— |
| 221 | CF$_3$, CH$_2$F | CH$_2$=CFCHF— |
| 222 | CF$_3$, CH$_2$F | CH$_2$=CHCF$_2$— |
| 223 | CF$_3$, CH$_2$F | CH$_2$=CHCH$_2$— |
| 224 | CF$_3$, CH$_2$F | CH$_2$=CHCHF— |
| 225 | CF$_3$, CH$_2$F | CH$_2$FCF=CF— |
| 226 | CF$_3$, CH$_2$F | CH$_2$FCF=CH— |
| 227 | CF$_3$, CH$_2$F | CH$_2$FCH=CF— |
| 228 | CF$_3$, CH$_2$F | CH$_2$FCH=CH— |
| 229 | CF$_3$, CH$_2$F | CH$_3$CF=CF— |
| 230 | CF$_3$, CH$_2$F | CH$_3$CF=CH— |
| 231 | CF$_3$, CH$_2$F | CH$_3$CH=CF— |
| 232 | CF$_3$, CH$_2$F | CH$_3$CH=CH— |
| 233 | CF$_3$, CH$_2$F | CF$_2$=CFCF$_2$CF$_2$— |
| 234 | CF$_3$, CH$_2$F | CF$_2$=CFCF$_2$CHF— |
| 235 | CF$_3$, CH$_2$F | CF$_2$=CFCF$_2$CH$_2$— |
| 236 | CF$_3$, CH$_2$F | CF$_2$=CFCHFCF$_2$— |
| 237 | CF$_3$, CH$_2$F | CF$_2$=CFCHFCHF— |
| 238 | CF$_3$, CH$_2$F | CF$_2$=CFCHFCH$_2$— |
| 239 | CF$_3$, CH$_2$F | CF$_2$=CFCH$_2$CF$_2$— |
| 240 | CF$_3$, CH$_2$F | CF$_2$=CFCH$_2$CHF— |
| 241 | CF$_3$, CH$_2$F | CF$_2$=CFCH$_2$CH$_2$— |
| 242 | CF$_3$, CH$_2$F | CF$_2$=CHCF$_2$CF$_2$— |
| 243 | CF$_3$, CH$_2$F | CF$_2$=CHCF$_2$CHF— |
| 244 | CF$_3$, CH$_2$F | CF$_2$=CFCF$_2$CH$_2$— |
| 245 | CF$_3$, CH$_2$F | CF$_2$=CHCHFCF$_2$— |
| 246 | CF$_3$, CH$_2$F | CF$_2$=CHCHFCHF— |
| 247 | CF$_3$, CH$_2$F | CF$_2$=CHCHFCH$_2$— |
| 248 | CF$_3$, CH$_2$F | CF$_2$=CHCH$_2$CF$_2$— |
| 249 | CF$_3$, CH$_2$F | CF$_2$=CHCH$_2$CHF— |
| 250 | CF$_3$, CH$_2$F | CF$_2$=CHCH$_2$CH$_2$— |
| 251 | CF$_3$, CH$_2$F | CHF=CFCF$_2$CF$_2$— |

TABLE I-continued

| Example | R | R' |
|---|---|---|
| 252 | CF$_3$, CH$_2$F | CHF=CFCF$_2$CHF— |
| 253 | CF$_3$, CH$_2$F | CHF=CFCF$_2$CH$_2$— |
| 254 | CF$_3$, CH$_2$F | CHF=CFCHFCF$_2$— |
| 255 | CF$_3$, CH$_2$F | CHF=CFCHFCHF— |
| 256 | CF$_3$, CH$_2$F | CHF=CFCHFCH$_2$— |
| 257 | CF$_3$, CH$_2$F | CHF=CFCH$_2$CF$_2$— |
| 258 | CF$_3$, CH$_2$F | CHF=CFCH$_2$CHF— |
| 259 | CF$_3$, CH$_2$F | CHF=CFCH$_2$CH$_2$— |
| 260 | CF$_3$, CH$_2$F | CHF=CHCF$_2$CF$_2$— |
| 261 | CF$_3$, CH$_2$F | CHF=CHCF$_2$CHF— |
| 262 | CF$_3$, CH$_2$F | CHF=CHCF$_2$CH$_2$— |
| 263 | CF$_3$, CH$_2$F | CHF=CHCHFCF$_2$— |
| 264 | CF$_3$, CH$_2$F | CHF=CHCHFCHF— |
| 265 | CF$_3$, CH$_2$F | CHF=CFCHFCH$_2$— |
| 266 | CF$_3$, CH$_2$F | CHF=CHCH$_2$CF$_2$— |
| 267 | CF$_3$, CH$_2$F | CHF=CHCH$_2$CHF— |
| 268 | CF$_3$, CH$_2$F | CHF=CHCH$_2$CH$_2$— |
| 269 | CF$_3$, CH$_2$F | CH$_2$=CFCF$_2$CF$_2$— |
| 270 | CF$_3$, CH$_2$F | CH$_2$=CFCF$_2$CHF— |
| 271 | CF$_3$, CH$_2$F | CH$_2$=CFCF$_2$CH$_2$— |
| 272 | CF$_3$, CH$_2$F | CH$_2$=CFCHFCF$_2$— |
| 273 | CF$_3$, CH$_2$F | CH$_2$=CFCHFCHF— |
| 274 | CF$_3$, CH$_2$F | CH$_2$=CFCHFCH$_2$— |
| 275 | CF$_3$, CH$_2$F | CH$_2$=CFCH$_2$CF$_2$— |
| 276 | CF$_3$, CH$_2$F | CH$_2$=CFCH$_2$CHF— |
| 277 | CF$_3$, CH$_2$F | CH$_2$=CFCH$_2$CH$_2$— |
| 278 | CF$_3$, CH$_2$F | CH$_2$=CHCF$_2$CF$_2$— |
| 279 | CF$_3$, CH$_2$F | CH$_2$=CHCF$_2$CHF— |
| 280 | CF$_3$, CH$_2$F | CH$_2$=CHCF$_2$CH$_2$— |
| 281 | CF$_3$, CH$_2$F | CH$_2$=CHCHFCF$_2$— |
| 282 | CF$_3$, CH$_2$F | CH$_2$=CHCHFCHF— |
| 283 | CF$_3$, CH$_2$F | CH$_2$=CHCHFCH$_2$— |
| 284 | CF$_3$, CH$_2$F | CH$_2$=CHCH$_2$CF$_2$— |
| 285 | CF$_3$, CH$_2$F | CH$_2$=CHCH$_2$CHF— |
| 286 | CF$_3$, CH$_2$F | CH$_2$=CHCH$_2$CH$_2$— |
| 287 | CF$_3$, CH$_2$F | CF$_3$CF=CFCF$_2$— |
| 288 | CF$_3$, CH$_2$F | CF$_3$CF=CFCHF— |
| 289 | CF$_3$, CH$_2$F | CF$_3$CF=CFCF$_2$— |
| 290 | CF$_3$, CH$_2$F | CF$_3$CF=CFCHF— |
| 291 | CF$_3$, CH$_2$F | CF$_3$CF=CFCH$_2$— |
| 292 | CF$_3$, CH$_2$F | CHF$_2$CF=CFCF$_2$— |
| 293 | CF$_3$, CH$_2$F | CHF$_2$CF=CFCHF— |
| 294 | CF$_3$, CH$_2$F | CHF$_2$CF=CFCH$_2$— |
| 295 | CF$_3$, CH$_2$F | CH$_2$FCF=CFCF$_2$— |
| 296 | CF$_3$, CH$_2$F | CH$_2$FCF=CFCHF— |
| 297 | CF$_3$, CH$_2$F | CH$_2$FCF=CFCH$_2$— |
| 298 | CF$_3$, CH$_2$F | CH$_3$CF=CFCF$_2$— |
| 299 | CF$_3$, CH$_2$F | CH$_3$CF=CFCHF— |
| 300 | CF$_3$, CH$_2$F | CH$_3$CF=CFCH$_2$— |
| 301 | CF$_3$, CH$_2$F | CF$_3$CF=CHCF$_2$— |
| 302 | CF$_3$, CH$_2$F | CF$_3$CF=CHCHF— |
| 303 | CF$_3$, CH$_2$F | CF$_3$CF=CHCH$_2$— |
| 304 | CF$_3$, CH$_2$F | CHF$_2$CF=CHCF$_2$— |
| 305 | CF$_3$, CH$_2$F | CHF$_2$CF=CHCHF— |
| 306 | CF$_3$, CH$_2$F | CHF$_2$CF=CHCH$_2$— |
| 307 | CF$_3$, CH$_2$F | CH$_2$FCF=CHCF$_2$— |
| 308 | CF$_3$, CH$_2$F | CH$_2$FCF=CHCHF— |
| 309 | CF$_3$, CH$_2$F | CH$_2$FCF=CHCH$_2$— |
| 310 | CF$_3$, CH$_2$F | CH$_3$CF=CHCF$_2$— |
| 311 | CF$_3$, CH$_2$F | CH$_3$CF=CHCHF— |
| 312 | CF$_3$, CH$_2$F | CH$_3$CF=CHCH$_2$— |
| 313 | CF$_3$, CH$_2$F | CF$_3$CH=CFCF$_2$— |
| 314 | CF$_3$, CH$_2$F | CF$_3$CH=CFCHF— |
| 315 | CF$_3$, CH$_2$F | CF$_3$CH=CFCH$_2$— |
| 316 | CF$_3$, CH$_2$F | CHF$_2$CH=CFCF$_2$— |
| 317 | CF$_3$, CH$_2$F | CHF$_2$CH=CFCHF— |
| 318 | CF$_3$, CH$_2$F | CHF$_2$CH=CFCH$_2$— |
| 319 | CF$_3$, CH$_2$F | CH$_2$FCH=CFCF$_2$— |
| 320 | CF$_3$, CH$_2$F | CH$_2$FCH=CFCHF— |
| 321 | CF$_3$, CH$_2$F | CH$_2$FCH=CFCH$_2$— |
| 322 | CF$_3$, CH$_2$F | CH$_3$CH=CFCF$_2$— |
| 323 | CF$_3$, CH$_2$F | CH$_3$CH=CFCHF— |
| 324 | CF$_3$, CH$_2$F | CH$_3$CH=CFCH$_2$— |
| 325 | CF$_3$, CH$_2$F | CF$_3$CH=CHCF$_2$— |
| 326 | CF$_3$, CH$_2$F | CF$_3$CH=CHCHF— |
| 327 | CF$_3$, CH$_2$F | CF$_3$CH=CHCH$_2$— |
| 328 | CF$_3$, CH$_2$F | CHF$_2$CH=CHCF$_2$— |
| 329 | CF$_3$, CH$_2$F | CHF$_2$CH=CHCHF— |
| 330 | CF$_3$, CH$_2$F | CHF$_2$CH=CHCH$_2$— |
| 331 | CF$_3$, CH$_2$F | CH$_2$FCH=CHCF$_2$— |
| 332 | CF$_3$, CH$_2$F | CH$_2$FCH=CHCHF— |

TABLE I-continued

| Example | R | R' |
|---|---|---|
| 333 | CF$_3$, CH$_2$F | CH$_2$FCH=CHCH$_2$— |
| 334 | CF$_3$, CH$_2$F | CH$_3$CH=CHCF$_2$— |
| 335 | CF$_3$, CH$_2$F | CH$_3$CH=CHCHF— |
| 336 | CF$_3$, CH$_2$F | CH$_3$CH=CHCH$_2$— |
| 337 | CF$_3$, CH$_2$F | CF$_3$CF$_2$CF=CF— |
| 338 | CF$_3$, CH$_2$F | CF$_3$CHFCF=CF— |
| 339 | CF$_3$, CH$_2$F | CF$_3$CH$_2$CF=CF— |
| 340 | CF$_3$, CH$_2$F | CHF$_2$CF$_2$CF=CF— |
| 341 | CF$_3$, CH$_2$F | CHF$_2$CHFCF=CF— |
| 342 | CF$_3$, CH$_2$F | CHF$_2$CH$_2$CF=CF— |
| 343 | CF$_3$, CH$_2$F | CH$_2$FF$_2$CF=CF— |
| 344 | CF$_2$, CH$_2$F | CH$_2$FCHFCF=CF— |
| 345 | CF$_3$, CH$_2$F | CH$_2$FCH$_2$CF=CF— |
| 346 | CF$_3$, CH$_2$F | CH$_3$CF$_2$CF=CF— |
| 347 | CF$_3$, CH$_2$F | CH$_3$CHFCF=CF— |
| 348 | CF$_3$, CH$_2$F | CH$_3$CH$_2$CF=CF— |
| 349 | CF$_3$, CH$_2$F | CF$_3$CF$_2$CF=CH— |
| 350 | CF$_3$, CH$_2$F | CF$_3$CHFCF=CH— |
| 351 | CF$_3$, CH$_2$F | CF$_3$CH$_2$CF=CH— |
| 352 | CF$_3$, CH$_2$F | CHF$_2$CF$_2$CF=CH— |
| 353 | CH$_3$, CH$_2$F | CHF$_2$CHFCF=CH— |
| 354 | CF$_3$, CH$_2$F | CHF$_2$CH$_2$CF=CH— |
| 355 | CF$_3$, CH$_2$F | CH$_2$FF$_2$CF=CH— |
| 356 | CF$_3$, CH$_2$F | CH$_2$FCHFCF=CH— |
| 357 | CF$_3$, CH$_2$F | CH$_2$FCH$_2$CF=CH— |
| 358 | CF$_3$, CH$_2$F | CH$_3$CF$_2$CF=CH— |
| 359 | CF$_3$, CH$_2$F | CH$_3$CHFCF=CH— |
| 360 | CF$_3$, CH$_2$F | CH$_3$CH$_2$CF=CH— |
| 361 | CF$_3$, CH$_2$F | CF$_3$CF$_2$CH=CF— |
| 362 | CF$_3$, CH$_2$F | CF$_3$CHFCH=CF— |
| 363 | CF$_3$, CH$_2$F | CF$_3$CH$_2$CH=CF— |
| 364 | CF$_3$, CH$_2$F | CHF$_2$CF$_2$CH=CF— |
| 365 | CF$_3$, CH$_2$F | CHF$_2$CHFCH=CF— |
| 366 | CF$_3$, CH$_2$F | CHF$_2$CH$_2$CH=CF— |
| 367 | CF$_3$, CH$_2$F | CH$_2$FF$_2$CH=CF— |
| 368 | CF$_3$, CH$_2$F | CH$_2$FCHFCH=CF— |
| 369 | CF$_3$, CH$_2$F | CH$_2$FCH$_2$CH=CF— |
| 370 | CF$_3$, CH$_2$F | CH$_3$CF$_2$CH=CF— |
| 371 | CF$_3$, CH$_2$F | CH$_3$CHFCH=CF— |
| 372 | CF$_3$, CH$_2$F | CH$_3$CH$_2$CH=CF— |
| 373 | CF$_3$, CH$_2$F | CF$_3$CF$_2$CH=CH— |
| 374 | CF$_3$, CH$_2$F | CF$_3$CHFCH=CH— |
| 375 | CF$_3$, CH$_2$F | CF$_3$CH$_2$CH=CH— |
| 376 | CF$_3$, CH$_2$F | CHF$_2$CF$_2$CH=CH— |
| 377 | CF$_3$, CH$_2$F | CHF$_2$CHFCH=CH— |
| 378 | CF$_3$, CH$_2$F | CHF$_2$CH$_2$CH=CH— |
| 379 | CF$_3$, CH$_2$F | CH$_2$FF$_2$CH=CH— |
| 380 | CF$_3$, CH$_2$F | CH$_2$FCHFCH=CH— |
| 381 | CF$_3$, CH$_2$F | CH$_2$FCH$_2$CH=CH— |
| 382 | CF$_3$, CH$_2$F | CH$_3$CF$_2$CH=CH— |
| 383 | CF$_3$, CH$_2$F | CH$_3$CHFCH=CH— |
| 384 | CF$_3$, CH$_2$F | CH$_3$CH$_2$CH=CH— |
| 385 | CF$_3$, CH$_3$CF$_2$ | CF$_2$=CF— |
| 386 | CF$_3$, CH$_3$CF$_2$ | CH$_2$=CH— |
| 387 | CF$_3$, CH$_3$CF$_2$ | CF$_2$=CFCF$_2$— |
| 388 | CF$_3$, CH$_3$CF$_2$ | CF$_2$=CFCH$_2$— |
| 389 | CF$_3$, CH$_3$CF$_2$ | CF$_2$=CFCHF— |
| 390 | CF$_3$, CH$_3$CF$_2$ | CF$_2$=CHCF$_2$— |
| 391 | CF$_3$, CH$_3$CF$_2$ | CF$_2$=CHCH$_2$— |
| 392 | CF$_3$, CH$_3$CF$_2$ | CF$_2$=CHCHF— |
| 393 | CF$_3$, CH$_3$CF$_2$ | CF$_3$CF=CF— |
| 394 | CF$_3$, CH$_3$CF$_2$ | CF$_3$CF=CH— |
| 395 | CF$_3$, CH$_3$CF$_2$ | CF$_3$CH=CF— |
| 396 | CF$_3$, CH$_3$CF$_2$ | CF$_3$CH=CH— |
| 397 | CF$_3$, CH$_3$CF$_2$ | CHF=CF— |
| 398 | CF$_3$, CH$_3$CF$_2$ | CHF=CH— |
| 399 | CF$_3$, CH$_3$CF$_2$ | CHF=CFCF$_2$— |
| 400 | CF$_3$, CH$_3$CF$_2$ | CHF=CFCH$_2$— |
| 401 | CF$_3$, CH$_3$CF$_2$ | CCHF=CFCHF— |
| 402 | CF$_3$, CH$_3$CF$_2$ | CHF=CHCF$_2$— |
| 403 | CF$_3$, CH$_3$CF$_2$ | CHF=CHCH$_2$— |
| 404 | CF$_3$, CH$_3$CF$_2$ | CHF=CHCHF— |
| 405 | CF$_3$, CH$_3$CF$_2$ | CHF$_2$CF=CF— |
| 406 | CF$_3$, CH$_3$CF$_2$ | CHF$_2$CF=CH— |
| 407 | CF$_3$, CH$_3$CF$_2$ | CHF$_2$CH=CF— |
| 408 | CF$_3$, CH$_3$CF$_2$ | CHF$_2$CH=CH— |
| 409 | CF$_3$, CH$_3$CF$_2$ | CH$_2$=CF— |
| 410 | CF$_3$, CH$_3$CF$_2$ | CH$_2$=CH— |
| 411 | CF$_3$, CH$_3$CF$_2$ | CH$_2$=CFCF$_2$— |
| 412 | CF$_3$, CH$_3$CF$_2$ | CH$_2$=CFCH$_2$— |
| 413 | CF$_3$, CH$_3$CF$_2$ | CH$_2$=CFCHF— |

TABLE I-continued

| Example | R | R' |
|---|---|---|
| 414 | CF₃, CH₃CF₂ | CH₂=CHCF₂— |
| 415 | CF₃, CH₃CF₂ | CH₂=CHCH₂— |
| 416 | CF₃, CH₃CF₂ | CH₂=CHCHF— |
| 417 | CF₃, CH₃CF₂ | CH₂FCF=CF— |
| 418 | CF₃, CH₃CF₂ | CH₂FCF=CH— |
| 419 | CF₃, CH₃CF₂ | CH₂FCH=CF— |
| 420 | CF₃, CH₃CF₂ | CH₂FCH=CH— |
| 421 | CF₃, CH₃CF₂ | CH₃CF=CF— |
| 422 | CF₃, CH₃CF₂ | CH₃CF=CH— |
| 423 | CF₃, CH₃CF₂ | CH₃CH=CF— |
| 424 | CF₃, CH₃CF₂ | CH₃CH=CH— |
| 425 | CF₃, CH₃CF₂ | CF₂=CFCF₂CF₂— |
| 426 | CF₃, CH₃CF₂ | CF₂=CFCF₂CHF— |
| 427 | CF₃, CH₃CF₂ | CF₂=CFCF₂CH₂— |
| 428 | CF₃, CH₃CF₂ | CF₂=CFCHFCF₂— |
| 429 | CF₃, CH₃CF₂ | CF₂=CFCHFCHF— |
| 430 | CF₃, CH₃CF₂ | CF₂=CFCHFCH₂— |
| 431 | CF₃, CH₃CF₂ | CF₂=CFCH₂CF₂— |
| 432 | CF₃, CH₃CF₂ | CF₂=CFCH₂CHF— |
| 433 | CF₃, CH₃CF₂ | CF₂=CFCH₂CH₂— |
| 434 | CF₃, CH₃CF₂ | CF₂=CHCF₂CF₂— |
| 435 | CF₃, CH₃CF₂ | CF₂=CHCF₂CHF— |
| 436 | CF₃, CH₃CF₂ | CF₂=CHCF₂CH₂— |
| 437 | CF₃, CH₃CF₂ | CF₂=CHCHFCF₂— |
| 438 | CF₃, CH₃CF₂ | CF₂=CHCHFCHF— |
| 439 | CF₃, CH₃CF₂ | CF₂=CHCHFCH₂— |
| 440 | CF₃, CH₃CF₂ | CF₂=CHCH₂CF₂— |
| 441 | CF₃, CH₃CF₂ | CF₂=CHCH₂CHF— |
| 442 | CF₃, CH₃CF₂ | CF₂=CHCH₂CH₂— |
| 443 | CF₃, CH₃CF₂ | CHF=CFCF₂CF₂— |
| 444 | CF₃, CH₃CF₂ | CHF=CFCF₂CHF— |
| 445 | CF₃, CH₃CF₂ | CHF=CFCF₂CH₂— |
| 446 | CF₃, CH₃CF₂ | CHF=CFCHFCF₂— |
| 447 | CF₃, CH₃CF₂ | CHF=CFCHFCHF— |
| 448 | CF₃, CH₃CF₂ | CHF=CFCHFCH₂— |
| 449 | CF₃, CH₃CF₂ | CHF=CFCH₂CF₂— |
| 450 | CF₃, CH₃CF₂ | CHF=CFCH₂CHF— |
| 451 | CF₃, CH₃CF₂ | CHF=CFCH₂CH₂— |
| 452 | CF₃, CH₃CF₂ | CHF=CHCF₂CF₂— |
| 453 | CF₃, CH₃CF₂ | CHF=CHCF₂CHF— |
| 454 | CF₃, CH₃CF₂ | CHF=CHCF₂CH₂— |
| 455 | CF₃, CH₃CF₂ | CHF=CHCHFCF₂— |
| 456 | CF₃, CH₃CF₂ | CHF=CHCHFCHF— |
| 457 | CF₃, CH₃CF₂ | CHF=CHCHFCH₂— |
| 458 | CF₃, CH₃CF₂ | CHF=CHCH₂CF₂— |
| 459 | CF₃, CH₃CF₂ | CHF=CHCH₂CHF— |
| 460 | CF₃, CH₃CF₂ | CHF=CHCH₂CH₂— |
| 461 | CF₃, CH₃CF₂ | CH₂=CFCF₂CF₂— |
| 462 | CF₃, CH₃CF₂ | CH₂=CFCF₂CHF— |
| 463 | CF₃, CH₃CF₂ | CH₂=CFCF₂CH₂— |
| 464 | CF₃, CH₃CF₂ | CH₂=CFCHFCF₂— |
| 465 | CF₃, CH₃CF₂ | CH₂=CFCHFCHF— |
| 466 | CF₃, CH₃CF₂ | CH₂=CFCHFCH₂— |
| 467 | CF₃, CH₃CF₂ | CH₂=CFCH₂CF₂— |
| 468 | CF₃, CH₃CF₂ | CH₂=CFCH₂CHF— |
| 469 | CF₃, CH₃CF₂ | CH₂=CFCH₂CH₂— |
| 470 | CF₃, CH₃CF₂ | CH₂=CHCF₂CF₂— |
| 471 | CF₃, CH₃CF₂ | CH₂=CHCF₂CHF— |
| 472 | CF₃, CH₃CF₂ | CH₂=CHCF₂CH₂— |
| 473 | CF₃, CH₃CF₂ | CH₂=CHCHFCF₂— |
| 474 | CF₃, CH₃CF₂ | CH₂=CHCHFCHF— |
| 475 | CF₃, CH₃CF₂ | CH₂=CHCHFCH₂— |
| 476 | CF₃, CH₃CF₂ | CH₂=CHCH₂CF₂— |
| 477 | CF₃, CH₃CF₂ | CH₂=CHCH₂CHF— |
| 478 | CF₃, CH₃CF₂ | CH₂=CHCH₂CH₂— |
| 479 | CF₃, CH₃CF₂ | CF₃CF=CFCF₂— |
| 480 | CF₃, CH₃CF₂ | CF₃CF=CFCHF— |
| 481 | CF₃, CH₃CF₂ | CF₃CF=CFCF₂— |
| 482 | CF₃, CH₃CF₂ | CF₃CF=CFCHF— |
| 483 | CF₃, CH₃CF₂ | CF₃CF=CFCH₂— |
| 484 | CF₃, CH₃CF₂ | CHF₂CF=CFCF₂— |
| 485 | CF₃, CH₃CF₂ | CHF₂CF=CFCHF— |
| 486 | CF₃, CH₃CF₂ | CHF₂CF=CFCH₂— |
| 487 | CF₃, CH₃CF₂ | CH₂FCF=CFCF₂— |
| 488 | CF₃, CH₃CF₂ | CH₂FCF=CFCHF— |
| 489 | CF₃, CH₃CF₂ | CH₂FCF=CFCH₂— |
| 490 | CF₃, CH₃CF₂ | CH₃CF=CFCF₂— |
| 491 | CF₃, CH₃CF₂ | CH₃CF=CFCHF— |
| 492 | CF₃, CH₃CF₂ | CH₃CF=CFCH₂— |
| 493 | CF₃, CH₃CF₂ | CF₃CF=CHCF₂— |
| 494 | CF₃, CH₃CF₂ | CF₃CF=CHCHF— |
| 495 | CF₃, CH₃CF₂ | CF₃CF=CHCH₂— |
| 496 | CF₃, CH₃CF₂ | CHF₂CF=CHCF₂— |
| 497 | CF₃, CH₃CF₂ | CHF₂CF=CHCHF— |
| 498 | CF₃, CH₃CF₂ | CHF₂CF=CHCH₂— |
| 499 | CF₃, CH₃CF₂ | CH₂FCF=CHCF₂— |
| 500 | CF₃, CH₃CF₂ | CH₂FCF=CHCHF— |
| 501 | CF₃, CH₃CF₂ | CH₂FCF=CHCH₂— |
| 502 | CF₃, CH₃CF₂ | CH₃CF=CHCF₂— |
| 503 | CF₃, CH₃CF₂ | CH₃CF=CHCHF— |
| 504 | CF₃, CH₃CF₂ | CH₃CF=CHCH₂— |
| 505 | CF₃, CH₃CF₂ | CF₃CH=CFCF₂— |
| 506 | CF₃, CH₃CF₂ | CF₃CH=CFCHF— |
| 507 | CF₃, CH₃CF₂ | CF₃CH=CFCH₂— |
| 508 | CF₃, CH₃CF₂ | CHF₂CH=CFCF₂— |
| 509 | CF₃, CH₃CF₂ | CHF₂CH=CFCHF— |
| 510 | CF₃, CH₃CF₂ | CHF₂CH=CFCH₂— |
| 511 | CF₃, CH₃CF₂ | CH₂FCH=CFCF₂— |
| 512 | CF₃, CH₃CF₂ | CH₂FCH=CFCHF— |
| 513 | CF₃, CH₃CF₂ | CH₂FCH=CFCH₂— |
| 514 | CF₃, CH₃CF₂ | CH₃CH=CFCF₂— |
| 515 | CF₃, CH₃CF₂ | CH₃CH=CFCHF— |
| 516 | CF₃, CH₃CF₂ | CH₃CH=CFCH₂— |
| 517 | CF₃, CH₃CF₂ | CF₃CH=CHCF₂— |
| 518 | CF₃, CH₃CF₂ | CH₃CH=CHCHF— |
| 519 | CF₃, CH₃CF₂ | CF₃CH=CHCH₂— |
| 520 | CF₃, CH₃CF₂ | CHF₂CH=CHCF₂— |
| 521 | CF₃, CH₃CF₂ | CHF₂CH=CHCHF— |
| 522 | CF₃, CH₃CF₂ | CHF₂CH=CHCH₂— |
| 523 | CF₃, CH₃CF₂ | CH₂FCH=CHCF₂— |
| 524 | CF₃, CH₃CF₂ | CH₂FCH=CHCHF— |
| 525 | CF₃, CH₃CF₂ | CH₂FCH=CHCH₂— |
| 526 | CF₃, CH₃CF₂ | CH₃CH=CHCF₂— |
| 527 | CF₃, CH₃CF₂ | CH₃CH=CHCHF— |
| 528 | CF₃, CH₃CF₂ | CH₃CH=CHCH₂— |
| 529 | CF₃, CH₃CF₂ | CF₃CF₂CF=CF— |
| 530 | CF₃, CH₃CF₂ | CF₃CHFCF=CF— |
| 531 | CF₃, CH₃CF₂ | CF₃CH₂CF=CF— |
| 532 | CF₃, CH₃CF₂ | CHF₂CF₂CF=CF— |
| 533 | CF₃, CH₃CF₂ | CHF₂CHFCF=CF— |
| 534 | CF₃, CH₃CF₂ | CHF₂CH₂CF=CF— |
| 535 | CF₃, CH₃CF₂ | CH₂FF₂CF=CF— |
| 536 | CF₃, CH₃CF₂ | CH₂FCHFCF=CF— |
| 537 | CF₃, CH₃CF₂ | CH₂FCH₂CF=CF— |
| 538 | CF₃, CH₃CF₂ | CH₃CF₂CF=CF— |
| 539 | CF₃, CH₃CF₂ | CH₃CHFCF=CF— |
| 540 | CF₃, CH₃CF₂ | CH₃CH₂CF=CF— |
| 541 | CF₃, CH₃CF₂ | CF₃CF₂CF=CH— |
| 542 | CF₃, CH₃CF₂ | CF₃CHFCF=CH— |
| 543 | CF₃, CH₃CF₂ | CF₃CH₂CF=CH— |
| 544 | CF₃, CH₃CF₂ | CHF₂CF₂CF=CH— |
| 545 | CF₃, CH₃CF₂ | CHF₂CHFCF=CH— |
| 546 | CF₃, CH₃CF₂ | CHF₂CH₂CF=CH— |
| 547 | CF₃, CH₃CF₂ | CH₂FF₂CF=CH— |
| 548 | CF₃, CH₃CF₂ | CH₂FCHFCF=CH— |
| 549 | CF₃, CH₃CF₂ | CH₂FCH₂CF=CH— |
| 550 | CF₃, CH₃CF₂ | CH₃CF₂CF=CH— |
| 551 | CF₃, CH₃CF₂ | CH₃CHFCF=CH— |
| 552 | CF₃, CH₃CF₂ | CH₃CH₂CF=CH— |
| 553 | CF₃, CH₃CF₂ | CF₃CF₂CH=CF— |
| 554 | CF₃, CH₃CF₂ | CF₃CHFCH=CF— |
| 555 | CF₃, CH₃CF₂ | CF₃CH₂CH=CF— |
| 556 | CF₃, CH₃CF₂ | CHF₂CF₂CH=CF— |
| 557 | CF₃, CH₃CF₂ | CHF₂CHFCH=CF— |
| 558 | CF₃, CH₃CF₂ | CHF₂CH₂CH=CF— |
| 559 | CF₃, CH₃CF₂ | CH₂FF₂CH=CF— |
| 560 | CF₃, CH₃CF₂ | CH₂FCHFCH=CF— |
| 561 | CF₃, CH₃CF₂ | CH₂FCH₂CH=CF— |
| 562 | CF₃, CH₃CF₂ | CH₃CF₂CH=CF— |
| 563 | CF₃, CH₃CF₂ | CH₃CHFCH=CF— |
| 564 | CF₃, CH₃CF₂ | CH₃CH₂CH=CF— |
| 565 | CF₃, CH₃CF₂ | CF₃CF₂CH=CH— |
| 566 | CF₃, CH₃CF₂ | CF₃CHFCH=CH— |
| 567 | CF₃, CH₃CF₂ | CF₃CH₂CH=CH— |
| 568 | CF₃, CH₃CF₂ | CHF₂CF₂CH=CH— |
| 569 | CF₃, CH₃CF₂ | CHF₂CHFCH=CH— |
| 570 | CF₃, CH₃CF₂ | CHF₂CH₂CH=CH— |
| 571 | CF₃, CH₃CF₂ | CH₂FF₂CH=CH— |
| 572 | CF₃, CH₃CF₂ | CH₂FCHFCH=CH— |
| 573 | CF₃, CH₃CF₂ | CH₂FCH₂CH=CH— |
| 574 | CF₃, CH₃CF₂ | CH₃CF₂CH=CH— |
| 575 | CF₃, CH₃CF₂ | CH₃CHFCH=CH— |

TABLE I-continued

| Example | R | R' |
|---|---|---|
| 576 | CF$_3$, CH$_3$CF$_2$ | CH$_3$CH$_2$CH=CH— |
| 577 | CHF$_2$, CH$_2$F | CF$_2$=CF— |
| 578 | CHF$_2$, CH$_2$F | CF$_2$=CH— |
| 579 | CHF$_2$, CH$_2$F | CF$_2$=CFCF$_2$— |
| 580 | CHF$_2$, CH$_2$F | CF$_2$=CFCH$_2$— |
| 581 | CHF$_2$, CH$_2$F | CF$_2$=CFCHF— |
| 582 | CHF$_2$, CH$_2$F | CF$_2$=CHCF$_2$— |
| 583 | CHF$_2$, CH$_2$F | CF$_2$=CHCH$_2$— |
| 584 | CHF$_2$, CH$_2$F | CF$_2$=CHCHF— |
| 585 | CHF$_2$, CH$_2$F | CF$_3$CF=CF— |
| 586 | CHF$_2$, CH$_2$F | CF$_3$CF=CH— |
| 587 | CHF$_2$, CH$_2$F | CF$_3$CH=CF— |
| 588 | CHF$_2$, CH$_2$F | CF$_3$CH=CH— |
| 589 | CHF$_2$, CH$_2$F | CHF=CF— |
| 590 | CHF$_2$, CH$_2$F | CHF=CH— |
| 591 | CHF$_2$, CH$_2$F | CHF=CFCF$_2$— |
| 592 | CHF$_2$, CH$_2$F | CHF=CFCH$_2$— |
| 593 | CHF$_2$, CH$_2$F | CHF=CFCHF— |
| 594 | CHF$_2$, CH$_2$F | CHF=CHCF$_2$— |
| 595 | CHF$_2$, CH$_2$F | CHF=CHCH$_2$— |
| 596 | CHF$_2$, CH$_2$F | CHF=CHCHF— |
| 597 | CHF$_2$, CH$_2$F | CHF$_2$CF=CF— |
| 598 | CHF$_2$, CH$_2$F | CHF$_2$CF=CH— |
| 599 | CHF$_2$, CH$_2$F | CHF$_2$CH=CF— |
| 600 | CHF$_2$, CH$_2$F | CHF$_2$CH=CH— |
| 601 | CHF$_2$, CH$_2$F | CH$_2$=CF— |
| 602 | CHF$_2$, CH$_2$F | CH$_2$=CH— |
| 603 | CHF$_2$, CH$_2$F | CH$_2$=CFCF$_2$— |
| 604 | CHF$_2$, CH$_2$F | CH$_2$=CFCH$_2$— |
| 605 | CHF$_2$, CH$_2$F | CH$_2$=CFCHF— |
| 606 | CHF$_2$, CH$_2$F | CH$_2$=CHCF$_2$— |
| 607 | CHF$_2$, CH$_2$F | CH$_2$=CHCH$_2$— |
| 608 | CHF$_2$, CH$_2$F | CH$_2$=CHCHF— |
| 609 | CHF$_2$, CH$_2$F | CH$_2$FCF=CF— |
| 610 | CHF$_2$, CH$_2$F | CH$_2$FCF=CH— |
| 611 | CHF$_2$, CH$_2$F | CH$_2$FCH=CF— |
| 612 | CHF$_2$, CH$_2$F | CH$_2$FCH=CH— |
| 613 | CHF$_2$, CH$_2$F | CH$_3$CF=CF— |
| 614 | CHF$_2$, CH$_2$F | CH$_3$CF=CH— |
| 615 | CHF$_2$, CH$_2$F | CH$_3$CH=CF— |
| 616 | CHF$_2$, CH$_2$F | CH$_3$CH=CH— |
| 617 | CHF$_2$, CH$_2$F | CF$_2$=CFCF$_2$CF$_2$— |
| 618 | CHF$_2$, CH$_2$F | CF$_2$=CFCF$_2$CHF— |
| 619 | CHF$_2$, CH$_2$F | CF$_2$=CFCF$_2$CH$_2$— |
| 620 | CHF$_2$, CH$_2$F | CF$_2$=CFCHFCF$_2$— |
| 621 | CHF$_2$, CH$_2$F | CF$_2$=CFCHFCHF— |
| 622 | CHF$_2$, CH$_2$F | CF$_2$=CFCHFCH$_2$— |
| 623 | CHF$_2$, CH$_2$F | CF$_2$=CFCH$_2$CF$_2$— |
| 624 | CHF$_2$, CH$_2$F | CF$_2$=CFCH$_2$CHF— |
| 625 | CHF$_2$, CH$_2$F | CF$_2$=CFCH$_2$CH$_2$— |
| 626 | CHF$_2$, CH$_2$F | CF$_2$=CHCF$_2$CF$_2$— |
| 627 | CHF$_2$, CH$_2$F | CF$_2$=CHCF$_2$CHF— |
| 628 | CHF$_2$, CH$_2$F | CF$_2$=CHCF$_2$CH$_2$— |
| 629 | CHF$_2$, CH$_2$F | CF$_2$=CHCHFCF$_2$— |
| 630 | CHF$_2$, CH$_2$F | CF$_2$=CHCHFCHF— |
| 631 | CHF$_2$, CH$_2$F | CF$_2$=CHCHFCH$_2$— |
| 632 | CHF$_2$, CH$_2$F | CF$_2$=CHCH$_2$CF$_2$— |
| 633 | CHF$_2$, CH$_2$F | CF$_2$=CHCH$_2$CHF— |
| 634 | CHF$_2$, CH$_2$F | CF$_2$=CHCH$_2$CH$_2$— |
| 635 | CHF$_2$, CH$_2$F | CHF=CFCF$_2$CF$_2$— |
| 636 | CHF$_2$, CH$_2$F | CHF=CFCF$_2$CHF— |
| 637 | CHF$_2$, CH$_2$F | CHF=CFCF$_2$CH$_2$— |
| 638 | CHF$_2$, CH$_2$F | CHF=CFCHFCF$_2$— |
| 639 | CHF$_2$, CH$_2$F | CHF=CFCHFCHF— |
| 640 | CHF$_2$, CH$_2$F | CHF=CFCHFCH$_2$— |
| 641 | CHF$_2$, CH$_2$F | CHF=CFCH$_2$CF$_2$— |
| 642 | CHF$_2$, CH$_2$F | CHF=CFCH$_2$CHF— |
| 643 | CHF$_2$, CH$_2$F | CHF=CFCH$_2$CH$_2$— |
| 644 | CHF$_2$, CH$_2$F | CHF=CHCF$_2$CF$_2$— |
| 645 | CHF$_2$, CH$_2$F | CHF=CHCF$_2$CHF— |
| 646 | CHF$_2$, CH$_2$F | CHF=CHCF$_2$CH$_2$— |
| 647 | CHF$_2$, CH$_2$F | CHF=CHCHFCF$_2$— |
| 648 | CHF$_2$, CH$_2$F | CHF=CHCHFCHF— |
| 649 | CHF$_2$, CH$_2$F | CHF=CHCHFCH$_2$— |
| 650 | CHF$_2$, CH$_2$F | CHF=CHCH$_2$CF$_2$— |
| 651 | CHF$_2$, CH$_2$F | CHF=CHCH$_2$CHF— |
| 652 | CHF$_2$, CH$_2$F | CHF=CHCH$_2$CH$_2$— |
| 653 | CHF$_2$, CH$_2$F | CH$_2$=CFCF$_2$CF$_2$— |
| 654 | CHF$_2$, CH$_2$F | CH$_2$=CFCF$_2$CHF— |
| 655 | CHF$_2$, CH$_2$F | CH$_2$=CFCF$_2$CH$_2$— |
| 656 | CHF$_2$, CH$_2$F | CH$_2$=CFCHFCF$_2$— |
| 657 | CHF$_2$, CH$_2$F | CH$_2$=CFCHFCHF— |
| 658 | CHF$_2$, CH$_2$F | CH$_2$=CFCHFCH$_2$— |
| 659 | CHF$_2$, CH$_2$F | CH$_2$=CFCH$_2$CF$_2$— |
| 660 | CHF$_2$, CH$_2$F | CH$_2$=CFCH$_2$CHF— |
| 661 | CHF$_2$, CH$_2$F | CH$_2$=CFCH$_2$CH$_2$— |
| 662 | CHF$_2$, CH$_2$F | CH$_2$=CHCF$_2$CF$_2$— |
| 663 | CHF$_2$, CH$_2$F | CH$_2$=CHCF$_2$CHF— |
| 664 | CHF$_2$, CH$_2$F | CH$_2$=CHCF$_2$CH$_2$— |
| 665 | CHF$_2$, CH$_2$F | CH$_2$=CHCHFCF$_2$— |
| 666 | CHF$_2$, CH$_2$F | CH$_2$=CHCHFCHF— |
| 667 | CHF$_2$, CH$_2$F | CH$_2$=CHCHFCH$_2$— |
| 668 | CHF$_2$, CH$_2$F | CH$_2$=CHCH$_2$CF$_2$— |
| 669 | CHF$_2$, CH$_2$F | CH$_2$=CHCH$_2$CHF— |
| 670 | CHF$_2$, CH$_2$F | CH$_2$=CHCH$_2$CH$_2$— |
| 671 | CHF$_2$, CH$_2$F | CF$_3$CF=CFCF$_2$— |
| 672 | CHF$_2$, CH$_2$F | CF$_3$CF=CFCHF— |
| 673 | CHF$_2$, CH$_2$F | CF$_3$CF=CFCF$_2$— |
| 674 | CHF$_2$, CH$_2$F | CF$_3$CF=CFCHF— |
| 677 | CHF$_2$, CH$_2$F | CF$_3$CF=CFCH$_2$— |
| 676 | CHF$_2$, CH$_2$F | CHF$_2$CF=CFCF$_2$— |
| 677 | CHF$_2$, CH$_2$F | CHF$_2$CF=CFCHF— |
| 678 | CHF$_2$, CH$_2$F | CHF$_2$CF=CFCH$_2$— |
| 679 | CHF$_2$, CH$_2$F | CH$_2$FCF=CFCF$_2$— |
| 680 | CHF$_2$, CH$_2$F | CH$_2$FCF=CFCHF— |
| 681 | CHF$_2$, CH$_2$F | CH$_2$FCF=CFCH$_2$— |
| 682 | CHF$_2$, CH$_2$F | CH$_3$CF=CFCF$_2$— |
| 683 | CHF$_2$, CH$_2$F | CH$_3$CF=CFCHF— |
| 684 | CHF$_2$, CH$_2$F | CH$_3$CF=CFCH$_2$— |
| 685 | CHF$_2$, CH$_2$F | CF$_3$CF=CHCF$_2$— |
| 686 | CHF$_2$, CH$_2$F | CF$_3$CF=CHCHF— |
| 687 | CHF$_2$, CH$_2$F | CF$_3$CF=CHCH$_2$— |
| 688 | CHF$_2$, CH$_2$F | CHF$_2$CF=CHCF$_2$— |
| 689 | CHF$_2$, CH$_2$F | CHF$_2$CF=CHCHF— |
| 690 | CHF$_2$, CH$_2$F | CHF$_2$CF=CHCH$_2$— |
| 691 | CHF$_2$, CH$_2$F | CH$_2$FCF=CHCF$_2$— |
| 692 | CHF$_2$, CH$_2$F | CH$_2$FCF=CHCHF— |
| 693 | CHF$_2$, CH$_2$F | CH$_2$FCF=CHCH$_2$— |
| 694 | CHF$_2$, CH$_2$F | CH$_3$CF=CHCF$_2$— |
| 695 | CHF$_2$, CH$_2$F | CH$_3$CF=CHCHF— |
| 696 | CHF$_2$, CH$_2$F | CH$_3$CF=CHCH$_2$— |
| 697 | CHF$_2$, CH$_2$F | CF$_3$CH=CFCF$_2$— |
| 698 | CHF$_2$, CH$_2$F | CF$_3$CH=CFCHF— |
| 699 | CHF$_2$, CH$_2$F | CF$_3$CH=CFCH$_2$— |
| 700 | CHF$_2$, CH$_2$F | CHF$_2$CH=CFCF$_2$— |
| 701 | CHF$_2$, CH$_2$F | CHF$_2$CH=CFCHF— |
| 702 | CHF$_2$, CH$_2$F | CHF$_2$CH=CFCH$_2$— |
| 703 | CHF$_2$, CH$_2$F | CH$_2$FCH=CFCF$_2$— |
| 704 | CHF$_2$, CH$_2$F | CH$_2$FCH=CFCHF— |
| 705 | CHF$_2$, CH$_2$F | CH$_2$FCH=CFCH$_2$— |
| 706 | CHF$_2$, CH$_2$F | CH$_3$CH=CFCF$_2$— |
| 707 | CHF$_2$, CH$_2$F | CH$_3$CH=CFCHF— |
| 708 | CHF$_2$, CH$_2$F | CH$_3$CH=CFCH$_2$— |
| 709 | CHF$_2$, CH$_2$F | CF$_3$CH=CHCF$_2$— |
| 710 | CHF$_2$, CH$_2$F | CF$_3$CH=CHCHF— |
| 711 | CHF$_2$, CH$_2$F | CF$_3$CH=CHCH$_2$— |
| 712 | CHF$_2$, CH$_2$F | CHF$_2$CH=CHCF$_2$— |
| 713 | CHF$_2$, CH$_2$F | CHF$_2$CH=CHCHF— |
| 714 | CHF$_2$, CH$_2$F | CHF$_2$CH=CHCH$_2$— |
| 715 | CHF$_2$, CH$_2$F | CH$_2$FCH=CHCF$_2$— |
| 716 | CHF$_2$, CH$_2$F | CH$_2$FCH=CHCHF— |
| 717 | CHF$_2$, CH$_2$F | CH$_2$FCH=CHCH$_2$— |
| 718 | CHF$_2$, CH$_2$F | CH$_3$CH=CHCF$_2$— |
| 719 | CHF$_2$, CH$_2$F | CH$_3$CH=CHCHF— |
| 720 | CHF$_2$, CH$_2$F | CH$_3$CH=CHCH$_2$— |
| 721 | CHF$_2$, CH$_2$F | CF$_3$CF$_2$CF=CF— |
| 722 | CHF$_2$, CH$_2$F | CF$_3$CHFCF=CF— |
| 723 | CHF$_2$, CH$_2$F | CF$_3$CH$_2$CF=CF— |
| 724 | CHF$_2$, CH$_2$F | CHF$_2$CF$_2$CF=CF— |
| 725 | CHF$_2$, CH$_2$F | CHF$_2$CHFCF=CF— |
| 726 | CHF$_2$, CH$_2$F | CHF$_2$CH$_2$CF=CF— |
| 727 | CHF$_2$, CH$_2$F | CH$_2$FF$_2$CF=CF— |
| 728 | CHF$_2$, CH$_2$F | CH$_2$FCHFCF=CF— |
| 729 | CHF$_2$, CH$_2$F | CH$_2$FCH$_2$CF=CF— |
| 730 | CHF$_2$, CH$_2$F | CH$_3$CF$_2$CF=CF— |
| 731 | CHF$_2$, CH$_2$F | CH$_3$CHFCF=CF— |
| 732 | CHF$_2$, CH$_2$F | CH$_3$CH$_2$CF=CF— |
| 733 | CHF$_2$, CH$_2$F | CF$_3$CF$_2$CF=CH— |
| 734 | CHF$_2$, CH$_2$F | CF$_3$CHFCF=CH— |
| 735 | CHF$_2$, CH$_2$F | CF$_3$CH$_2$CF=CH— |
| 736 | CHF$_2$, CH$_2$F | CHF$_2$CF$_2$CF=CH— |
| 737 | CHF$_2$, CH$_2$F | CHF$_2$CHFCF=CH— |

TABLE I-continued

| Example | R | R' |
|---|---|---|
| 738 | CHF$_2$, CH$_2$F | CHF$_2$CH$_2$CF=CH— |
| 739 | CHF$_2$, CH$_2$F | CH$_2$FF$_2$CF=CH— |
| 740 | CHF$_2$, CH$_2$F | CH$_2$FCHFCF=CH— |
| 741 | CHF$_2$, CH$_2$F | CH$_2$FCH$_2$CF=CH— |
| 742 | CHF$_2$, CH$_2$F | CH$_3$CF$_2$CF=CH— |
| 743 | CHF$_2$, CH$_2$F | CH$_3$CHFCF=CH— |
| 744 | CHF$_2$, CH$_2$F | CH$_3$CH$_2$CF=CH— |
| 745 | CHF$_2$, CH$_2$F | CF$_3$CF$_2$CH=CF— |
| 746 | CHF$_2$, CH$_2$F | CF$_3$CHFCH=CF— |
| 747 | CHF$_2$, CH$_2$F | CF$_3$CH$_2$CH=CF— |
| 748 | CHF$_2$, CH$_2$F | CHF$_2$CF$_2$CH=CF— |
| 749 | CHF$_2$, CH$_2$F | CHF$_2$CHFCH=CF— |
| 750 | CHF$_2$, CH$_2$F | CHF$_2$CH$_2$CH=CF— |
| 751 | CHF$_2$, CH$_2$F | CH$_2$FF$_2$CH=CF— |
| 752 | CHF$_2$, CH$_2$F | CH$_2$FCHFCH=CF— |
| 753 | CHF$_2$, CH$_2$F | CH$_2$FCH$_2$CH=CF— |
| 754 | CHF$_2$, CH$_2$F | CH$_3$CF$_2$CH=CF— |
| 755 | CHF$_2$, CH$_2$F | CH$_3$CHFCH=CF— |
| 756 | CHF$_2$, CH$_2$F | CH$_3$CH$_2$CH=CF— |
| 757 | CHF$_2$, CH$_2$F | CF$_3$CF$_2$CH=CH— |
| 758 | CHF$_2$, CH$_2$F | CF$_3$CHFCH=CH— |
| 759 | CHF$_2$, CH$_2$F | CF$_3$CH$_2$CH=CH— |
| 760 | CHF$_2$, CH$_2$F | CHF$_2$CF$_2$CH=CH— |
| 761 | CHF$_2$, CH$_2$F | CHF$_2$CHFCH=CH— |
| 762 | CHF$_2$, CH$_2$F | CHF$_2$CH$_2$CH=CH— |
| 763 | CHF$_2$, CH$_2$F | CH$_2$FF$_2$CH=CH— |
| 764 | CHF$_2$, CH$_2$F | CH$_2$FCHFCH=CH— |
| 765 | CHF$_2$, CH$_2$F | CH$_2$FCH$_2$CH=CH— |
| 766 | CHF$_2$, CH$_2$F | CH$_3$CF$_2$CH=CH— |
| 767 | CHF$_2$, CH$_2$F | CH$_3$CHFCH=CH— |
| 768 | CHF$_2$, CH$_2$F | CH$_3$CH$_2$CH=CH— |
| 769 | CF$_3$, CF$_3$ | CF$_2$=CF— |
| 770 | CF$_3$, CF$_3$ | CF$_2$=CH— |
| 771 | CF$_3$, CF$_3$ | CF$_2$=CFCF$_2$— |
| 772 | CF$_3$, CF$_3$ | CF$_2$=CFCH$_2$— |
| 773 | CF$_3$, CF$_3$ | CF$_2$=CFCHF— |
| 774 | CF$_3$, CF$_3$ | CF$_2$=CHCF$_2$— |
| 775 | CF$_3$, CF$_3$ | CF$_2$=CHCH$_2$— |
| 776 | CF$_3$, CF$_3$ | CF$_2$=CHCHF— |
| 777 | CF$_3$, CF$_3$ | CF$_3$CF=CF— |
| 778 | CF$_3$, CF$_3$ | CF$_3$CF=CH— |
| 779 | CF$_3$, CF$_3$ | CF$_3$CH=CF— |
| 780 | CF$_3$, CF$_3$ | CF$_3$CH=CH— |
| 781 | CF$_3$, CF$_3$ | CHF=CF— |
| 782 | CF$_3$, CF$_3$ | CHF=CH— |
| 783 | CF$_3$, CF$_3$ | CHF=CFCF$_2$— |
| 784 | CF$_3$, CF$_3$ | CHF=CFCH$_2$— |
| 785 | CF$_3$, CF$_3$ | CHF=CFCHF— |
| 786 | CF$_3$, CF$_3$ | CHF=CHCF$_2$— |
| 787 | CF$_3$, CF$_3$ | CHF=CHCH$_2$— |
| 788 | CF$_3$, CH$_3$ | CHF=CHCHF— |
| 789 | CF$_3$, CF$_3$ | CHF$_2$CF=CF— |
| 790 | CF$_3$, CF$_3$ | CHF$_2$CF=CH— |
| 791 | CF$_3$, CF$_3$ | CHF$_2$CH=CF— |
| 792 | CF$_3$, CF$_3$ | CHF$_2$CH=CH— |
| 793 | CF$_3$, CF$_3$ | CH$_2$=CF— |
| 794 | CF$_3$, CF$_3$ | CH$_2$=CH— |
| 795 | CF$_3$, CF$_3$ | CH$_2$=CFCF— |
| 796 | CF$_3$, CF$_3$ | CH$_2$=CFCH$_2$— |
| 797 | CF$_3$, CF$_3$ | CH$_2$=CFCHF— |
| 798 | CF$_3$, CF$_3$ | CH$_2$=CHCF$_2$— |
| 799 | CF$_3$, CF$_3$ | CH$_2$=CHCH$_2$— |
| 800 | CF$_3$, CF$_3$ | CH$_2$=CHCHF— |
| 801 | CF$_3$, CF$_3$ | CH$_2$FCF=CF— |
| 802 | CF$_3$, CF$_3$ | CH$_2$FCF=CH— |
| 803 | CF$_3$, CF$_3$ | CH$_2$FCH=CF— |
| 804 | CF$_3$, CF$_3$ | CH$_2$FCH=CH— |
| 805 | CF$_3$, CF$_3$ | CH$_3$CF=CF— |
| 806 | CF$_3$, CF$_3$ | CH$_3$CF=CH— |
| 807 | CF$_3$, CF$_3$ | CH$_3$CH=CF— |
| 808 | CF$_3$, CF$_3$ | CH$_3$CH=CH— |
| 809 | CF$_3$, CF$_3$ | CF$_2$=CFCF$_2$CF$_2$— |
| 810 | CF$_3$, CF$_3$ | CF$_2$=CFCF$_2$CHF— |
| 811 | CF$_3$, CF$_3$ | CF$_2$=CFCF$_2$CH$_2$— |
| 812 | CF$_3$, CF$_3$ | CF$_2$=CFCHFCF$_2$— |
| 813 | CF$_3$, CF$_3$ | CF$_2$=CFCHFCHF— |
| 814 | CF$_3$, CF$_3$ | CF$_2$=CFCHFCH$_2$— |
| 815 | CF$_3$, CF$_3$ | CF$_2$=CFCH$_2$CF$_2$— |
| 816 | CF$_3$, CF$_3$ | CF$_2$=CFCH$_2$CHF— |
| 817 | CF$_3$, CF$_3$ | CF$_2$=CFCH$_2$CH$_2$— |
| 818 | CF$_3$, CF$_3$ | CF$_2$=CHCF$_2$CF$_2$— |
| 819 | CF$_3$, CF$_3$ | CF$_2$=CHCF$_2$CHF— |
| 820 | CF$_3$, CF$_3$ | CF$_2$=CHCF$_2$CH$_2$— |
| 821 | CF$_3$, CF$_3$ | CF$_2$=CHCHFCF$_2$— |
| 822 | CF$_3$, CF$_3$ | CF$_2$=CHCHFCHF— |
| 823 | CF$_3$, CF$_3$ | CF$_2$=CHCHFCH$_2$— |
| 824 | CF$_3$, CF$_3$ | CF$_2$=CHCH$_2$CF$_2$— |
| 825 | CF$_3$, CF$_3$ | CF$_2$=CHCH$_2$CHF— |
| 826 | CF$_3$, CF$_3$ | CF$_2$=CHCH$_2$CH$_2$— |
| 827 | CF$_3$, CF$_3$ | CHF=CFCF$_2$CF$_2$— |
| 828 | CF$_3$, CF$_3$ | CHF=CFCF$_2$CHF— |
| 829 | CF$_3$, CF$_2$ | CHF=CFCF$_2$CH$_2$— |
| 830 | CF$_3$, CF$_3$ | CHF=CFCHFCF$_2$— |
| 831 | CF$_3$, CF$_3$ | CHF=CFCHFCHF— |
| 832 | CF$_3$, CF$_3$ | CHF=CFCHFCH$_2$— |
| 833 | CF$_3$, CF$_3$ | CHF=CFCH$_2$CF$_2$— |
| 834 | CF$_3$, CF$_3$ | CHF=CFCH$_2$CHF— |
| 835 | CF$_3$, CF$_3$ | CHF=CFCH$_2$CH$_2$— |
| 836 | CF$_3$, CF$_3$ | CHF=CHCF$_2$CF$_2$— |
| 837 | CF$_3$, CF$_3$ | CHF=CHCF$_2$CHF— |
| 838 | CF$_3$, CF$_3$ | CHF=CHCF$_2$CH$_2$— |
| 839 | CF$_3$, CF$_3$ | CHF=CHCHFCF$_2$— |
| 840 | CF$_3$, CF$_3$ | CHF=CHCHFCHF— |
| 841 | CF$_3$, CF$_3$ | CHF=CHCHFCH$_2$— |
| 842 | CF$_3$, CF$_3$ | CHF=CHCH$_2$CF$_2$— |
| 843 | CF$_3$, CF$_3$ | CHF=CHCH$_2$CHF— |
| 844 | CF$_3$, CF$_3$ | CHF=CHCH$_2$CH$_2$— |
| 845 | CF$_3$, CF$_3$ | CH$_2$=CFCF$_2$CF$_2$— |
| 846 | CF$_3$, CF$_3$ | CH$_2$=CFCF$_2$CHF— |
| 847 | CF$_3$, CF$_3$ | CH$_2$=CFCF$_2$CH$_2$— |
| 848 | CF$_3$, CF$_3$ | CH$_2$=CFCHFCF$_2$— |
| 849 | CF$_3$, CF$_3$ | CH$_2$=CFCHFCHF— |
| 850 | CF$_3$, CF$_3$ | CH$_2$=CFCHFCH$_2$— |
| 851 | CF$_3$, CF$_3$ | CH$_2$=CFCH$_2$CF$_2$— |
| 852 | CF$_3$, CF$_3$ | CH$_2$=CFCH$_2$CHF— |
| 853 | CF$_3$, CF$_3$ | CH$_2$=CFCH$_2$CH$_2$— |
| 854 | CF$_3$, CF$_3$ | CH$_2$=CHCF$_2$CF$_2$— |
| 855 | CF$_3$, CF$_3$ | CH$_2$=CHCF$_2$CHF— |
| 856 | CF$_2$, CF$_3$ | CH$_2$=CHCF$_2$CH$_2$— |
| 857 | CF$_3$, CF$_3$ | CH$_2$=CHCHFCF$_2$— |
| 858 | CF$_3$, CF$_3$ | CH$_2$=CHCHFCHF— |
| 859 | CF$_3$, CF$_3$ | CH$_2$=CHCHFCH$_2$— |
| 860 | CF$_3$, CF$_3$ | CH$_2$=CHCH$_2$CF$_2$— |
| 861 | CF$_3$, CF$_3$ | CH$_2$=CHCH$_2$CHF— |
| 862 | CF$_3$, CF$_3$ | CH$_2$=CHCH$_2$CH$_2$— |
| 863 | CF$_3$, CF$_3$ | CF$_3$CF=CFCF$_2$— |
| 864 | CF$_3$, CF$_3$ | CF$_3$CF=CFCHF— |
| 865 | CF$_3$, CF$_3$ | CF$_3$CF=CFCF$_2$— |
| 866 | CF$_3$, CF$_3$ | CF$_3$CF=CFCHF— |
| 867 | CF$_3$, CF$_3$ | CF$_3$CF=CFCH$_2$— |
| 868 | CF$_3$, CF$_3$ | CHF$_2$CF=CFCF$_2$— |
| 869 | CF$_3$, CF$_3$ | CHF$_2$CF=CFCHF— |
| 870 | CF$_3$, CF$_3$ | CHF$_2$CF=CFCH$_2$— |
| 871 | CF$_3$, CF$_3$ | CH$_2$FCF=CFCF$_2$— |
| 872 | CF$_3$, CF$_3$ | CH$_2$FCF=CFCHF— |
| 873 | CF$_3$, CF$_3$ | CH$_2$FCF=CFCH$_2$— |
| 874 | CF$_3$, CF$_3$ | CH$_3$CF=CFCF$_2$— |
| 875 | CF$_3$, CF$_3$ | CH$_3$CF=CFCHF— |
| 876 | CF$_3$, CF$_3$ | CH$_3$CF=CFCH$_2$— |
| 877 | CF$_3$, CF$_3$ | CF$_3$CF=CHCF$_2$— |
| 878 | CF$_3$, CF$_3$ | CF$_3$CF=CHCHF— |
| 879 | CF$_3$, CF$_3$ | CF$_3$CF=CHCH$_2$— |
| 880 | CF$_3$, CF$_3$ | CHF$_2$CF=CHCF$_2$— |
| 881 | CF$_3$, CF$_3$ | CHF$_2$CF=CHCHF— |
| 882 | CF$_3$, CF$_3$ | CHF$_2$CF=CHCH$_2$— |
| 883 | CF$_3$, CF$_3$ | CH$_2$FCF=CHCF$_2$— |
| 884 | CF$_3$, CF$_3$ | CH$_2$FCF=CHCHF— |
| 885 | CF$_3$, CF$_3$ | CH$_2$FCF=CHCH$_2$— |
| 886 | CF$_3$, CF$_3$ | CH$_3$CF=CHCF$_2$— |
| 887 | CF$_3$, CF$_3$ | CH$_3$CF=CHCHF— |
| 888 | CF$_3$, CF$_3$ | CH$_3$CF=CHCH$_2$— |
| 889 | CF$_3$, CF$_3$ | CF$_3$CH=CFCF$_2$— |
| 890 | CF$_3$, CF$_3$ | CF$_3$CH=CFCHF— |
| 891 | CF$_3$, CF$_3$ | CF$_3$CH=CFCH$_2$— |
| 892 | CF$_3$, CF$_3$ | CHF$_2$CH=CFCF$_2$— |
| 893 | CF$_3$, CF$_3$ | CHF$_2$CH=CFCHF— |
| 894 | CF$_3$, CF$_3$ | CHF$_2$CH=CFCH$_2$— |
| 895 | CF$_3$, CF$_3$ | CH$_2$FCH=CFCF$_2$— |
| 896 | CF$_3$, CF$_3$ | CH$_2$FCH=CFCHF— |
| 897 | CF$_3$, CF$_3$ | CH$_2$FCH=CFCH$_2$— |
| 898 | CF$_3$, CF$_3$ | CH$_3$CH=CFCF$_2$— |
| 899 | CF$_3$, CF$_3$ | CH$_3$CH=CFCHF— |

TABLE I-continued

| Example | R | R' |
|---|---|---|
| 900 | CF$_3$, CF$_3$ | CH$_3$CH=CFCH$_2$— |
| 901 | CF$_3$, CF$_3$ | CF$_3$CH=CHCF$_2$— |
| 902 | CF$_3$, CF$_3$ | CF$_3$CH=CHCHF— |
| 903 | CF$_3$, CF$_3$ | CF$_3$CH=CHCH$_2$— |
| 904 | CF$_3$, CF$_3$ | CHF$_2$CH=CHCF$_2$— |
| 905 | CF$_3$, CF$_3$ | CHF$_2$CH=CHCHF— |
| 906 | CF$_3$, CF$_3$ | CHF$_2$CH=CHCH$_2$— |
| 907 | CF$_3$, CF$_3$ | CH$_2$FCH=CHCF$_2$— |
| 908 | CF$_3$, CF$_3$ | CH$_2$FCH=CHCHF— |
| 909 | CF$_3$, CF$_3$ | CH$_2$FCH=CHCH$_2$— |
| 910 | CF$_3$, CF$_3$ | CH$_3$CH=CHCF$_2$— |
| 911 | CF$_3$, CF$_3$ | CH$_3$CH=CHCHF— |
| 912 | CF$_3$, CF$_3$ | CH$_3$CH=CHCH$_2$— |
| 913 | CF$_3$, CF$_3$ | CF$_3$CF$_2$CF=CF— |
| 914 | CF$_3$, CF$_3$ | CF$_3$CHFCF=CF— |
| 915 | CF$_3$, CF$_3$ | CF$_3$CH$_2$CF=CF— |
| 916 | CF$_3$, CF$_3$ | CHF$_2$CF$_2$CF=CF— |
| 917 | CF$_3$, CF$_3$ | CHF$_2$CHFCF=CF— |
| 918 | CF$_3$, CF$_3$ | CHF$_2$CH$_2$CF=CF— |
| 919 | CF$_3$, CF$_3$ | CH$_2$FF$_2$CF=CF— |
| 920 | CF$_3$, CF$_3$ | CH$_2$FCHFCF=CF— |
| 921 | CF$_3$, CF$_3$ | CH$_2$FCH$_2$CF=CF— |
| 922 | CF$_3$, CF$_3$ | CH$_3$CF$_2$CF=CF— |
| 923 | CF$_3$, CF$_3$ | CH$_3$CHFCF=CF— |
| 924 | CF$_3$, CF$_3$ | CH$_3$CH$_2$CF=CF— |
| 925 | CF$_3$, CF$_3$ | CF$_3$CF$_2$CF=CH— |
| 926 | CF$_3$, CF$_3$ | CF$_3$CHFCF=CH— |
| 927 | CF$_3$, CF$_3$ | CF$_3$CH$_2$CF=CH— |
| 928 | CF$_3$, CF$_3$ | CHF$_2$CF$_2$CF=CH— |
| 929 | CF$_3$, CF$_3$ | CHF$_2$CHFCF=CH— |
| 930 | CF$_3$, CF$_3$ | CHF$_2$CH$_2$CF=CH— |
| 931 | CF$_3$, CF$_3$ | CH$_2$FF$_2$CF=CH— |
| 932 | CF$_3$, CF$_3$ | CH$_2$FCHFCF=CH— |
| 933 | CF$_3$, CF$_3$ | CH$_2$FCH$_2$CF=CH— |
| 934 | CF$_3$, CF$_3$ | CH$_3$CF$_2$CF=CH— |
| 935 | CF$_3$, CF$_3$ | CH$_3$CHFCF=CH— |
| 936 | CF$_3$, CF$_3$ | CH$_3$CH$_2$CF=CH= |
| 937 | CF$_3$, CF$_3$ | CF$_3$CF$_2$CH=CF— |
| 938 | CF$_3$, CF$_3$ | CF$_3$CHFCH=CF— |
| 939 | CF$_3$, CF$_3$ | CF$_3$CH$_2$CH=CF— |
| 940 | CF$_3$, CF$_3$ | CHF$_2$CF$_2$CH=CF— |
| 941 | CF$_3$, CF$_3$ | CHF$_2$CHFCH=CF— |
| 942 | CF$_3$, CF$_3$ | CHF$_2$CH$_2$CH=CF— |
| 943 | CF$_3$, CF$_3$ | CH$_2$FF$_2$CH=CF— |
| 944 | CF$_3$, CF$_3$ | CH$_2$FCHFCH=CF— |
| 945 | CF$_3$, CF$_3$ | CH$_2$FCH$_2$CH=CF— |
| 946 | CF$_3$, CF$_3$ | CH$_3$CF$_2$CH=CF— |
| 947 | CF$_3$, CF$_3$ | CH$_3$CHFCH=CF— |
| 948 | CF$_3$, CF$_3$ | CH$_3$CH$_2$CH=CF— |
| 949 | CF$_3$, CF$_3$ | CF$_3$CF$_2$CH=CH— |
| 950 | CF$_3$, CF$_3$ | CF$_3$CHFCH=CH— |
| 951 | CF$_3$, CF$_3$ | CF$_3$CH$_2$CH=CH— |
| 952 | CF$_3$, CF$_3$ | CHF$_2$CF$_2$CH=CH— |
| 953 | CF$_3$, CF$_3$ | CHF$_2$CHFCH=CH— |
| 954 | CF$_3$, CF$_3$ | CHF$_2$CH$_2$CH=CH— |
| 955 | CF$_3$, CF$_3$ | CH$_2$FF$_2$CH=CH— |
| 956 | CF$_3$, CF$_3$ | CH$_2$FCHFCH=CH— |
| 957 | CF$_3$, CF$_3$ | CH$_2$FCH$_2$CH=CH— |
| 958 | CF$_3$, CF$_3$ | CH$_3$CF$_2$CH=CH— |
| 959 | CF$_3$, CF$_3$ | CH$_3$CHFCH=CH— |
| 960 | CF$_3$, CF$_3$ | CH$_3$CH$_2$CH=CH— |

EXAMPLES 961-1,152

The novel compounds of these Examples have the same R') groups as Examples 1-192 but instead, the two R groups are CHF$_2$, and CH$_3$CF$_2$.

EXAMPLES 1,153-1,344

The novel compounds of the Examples have the same R' groups as Examples 1-192 but instead, the two R groups are CH$_2$F and CH$_3$CF$_2$.

EXAMPLES 1,345-1,536

The novel compounds of these Examples have the same R' groups as Examples 1-192 but instead, the two R groups are CHF$_2$ and CHF$_2$.

EXAMPLES 1,537-1,728

The novel compounds of these Examples have the same R' groups as Examples 1-192 but instead, the two R groups are CH$_2$F and CH$_2$F.

EXAMPLES 1,729-1,920

The novel compounds of these Examples have the same R' groups as Examples 1-192 but instead, the two R groups are CH$_3$CF$_2$ and CH$_3$CF$_2$.

EXAMPLES 1.921-3,840

Metal coupons are soiled with various types of oil. The soiled metal coupons are immersed in the novel solvents of Table I above for a period of 15 seconds to 2 minutes, removed, and allowed to air dry. Upon visual inspection, the soil appears to be substantially removed.

EXAMPLES 3,841-5,760

Metal coupons are soiled with various types of oil. The soiled metal coupons are wiped with the novel solvents of Table I above and allowed to air dry. Upon visual inspection, the soil appears to be substantially removed.

Having described the invention in detail and by reference to Preferred embodiments thereof, it will be apparent that modifications and variations are possible without departing from the scope of the invention defined in the appended claims.

What is claimed is:

1. A compound having the formula

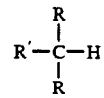

wherein each R is the same or different and is selected from the group consisting of CF$_3$, CHF$_2$, CH$_2$F, and CH$_3$CF$_2$, and R' is an alkenyl or fluoroalkenyl group having 2 to 6 carbon atoms.

2. The compound of claim 1 wherein said R' is selected from the group consisting of CF$_2$=CF—, CF$_2$=CH—, CF$_2$=CFCF$_2$—, CF$_2$=CFCH$_2$—, CF$_2$=CFCHF—, CF$_2$CHCF$_2$—, CF$_2$=CHCH$_2$—, CF$_2$=CHCHF—, CF$_3$CF=CF—, CF$_3$CF=CH—, CF$_3$CH=CF—, CF$_3$CH=CH—, CHF=CF—, CHF=CH—, CHF=CFCF$_2$—, CHF=CFCH$_2$—, CHF=CFCHF—, CHF=CHCF$_2$—, CHF=CHCH$_2$—, CHF=CHCHF—, CHF$_2$CF=CF—, CHF$_2$CF=CH—, CHF$_2$CH=CF—, CHF$_2$CH=CH—, CH$_2$=CF—, CH$_2$=CH—, CH$_2$=CHCF$_2$—, CH$_2$=CHCH$_2$—, CH$_2$=CHCHF—, CH$_2$FCF=CF—, CH$_2$FCF=CH—, CH$_2$FCH=CF—, and CH$_2$FCH=CH—CF$_3$.

3. The compound of claim 1 wherein said R' is selected from the group consisting of CH$_3$CF=CF—, CH$_3$CF=CH—, CH$_3$CH=CF—, CH$_3$CH=CH—, CF$_2$=CFCF , CF$_2$=CFCF$_2$CHF—, CF$_2$=CFCF , CF$_2$=CFCHFCF$_2$—, CF$_2$=CFCHFCHF—, CF$_2$=CFCHFCH$_2$—, CF$_2$=CFCH CF$_2$=CFCH$_2$CHF—, CF$_2$=CHCF$_2$CHF—, CF$_2$=CHCF
CF$_2$=CHCF$_2$CHF—,
CF$_2$=CHCHFCF$_2$—,
CF$_2$=CHCHFCH$_2$—,
CF$_2$=CHCH$_2$CHF—,
CHF=CFCF$_2$CF$_2$—,
CHF=CFCF$_2$CH$_2$—,
CHF=CFCHFCHF—,
CHF=CFCH$_2$CF$_2$—,
CHF=CFCH$_2$CH$_2$—,
CHF=CHCF$_2$CHF—,
CHF=CHCHFCF$_2$—,
CHF=CHCHFCH$_2$—,
CHF=CHCH$_2$CHF—,
CH$_2$=CFCF$_2$CF$_2$—,
CH$_2$=CFCF$_2$CH$_2$—,
CH$_2$=CFCHFCHF—,
CH$_2$=CFCH$_2$CF$_2$—,
CH$_2$=CFCH$_2$CH$_2$—,
CH$_2$CHCF$_2$CHF—,
CH$_2$=CHCHFCF$_2$—,
CH$_2$=CHCHFCH$_2$—,
CH$_2$=CHCH$_2$CHF—, and
CF$_2$=CHCHFCF$_2$—,
CF$_2$=CHCF$_2$CH$_2$—,
CF$_2$=CHCHFCHF—,
CF$_2$=CHCH$_2$CF$_2$—,
CF$_2$=CHCH$_2$CH$_2$—,
CHF=CFCF$_2$CHF—,
CHF=CFCHFCF$_2$—,
CHF=CFCHFCH$_2$—,
CHF=CFCH$_2$CHF—,
CHF=CHCF$_2$CF$_2$—,
CHF=CHCF$_2$CH$_2$—,
CHF=CHCHFCHF—,
CHF=CHCH$_2$CF$_2$—,
CHF=CHCH$_2$CH$_2$—,
CH$_2$=CFCF$_2$CHF—,
CH$_2$=CFCHFCF$_2$—,
CH$_2$=CFCHFCH$_2$—,
CH$_2$=CFCH$_2$CHF—,
CH$_2$=CHCF$_2$CF$_2$—,
CH$_2$=CHCF$_2$CH$_2$—,
CH$_2$=CHCHFCHF—,
CH$_2$=CHCH$_2$CF$_2$—,
CH$_2$=CHCH$_2$CH$_2$—.

4. The compound of claim 1 wherein said R') is selected from the group consisting of CF$_3$CF=CFCF$_2$—, CF$_3$CF=CFCHF—,
CHF$_2$CF=CFCF$_2$—,
CHF$_2$CF=CFCH$_2$—,
CH$_2$FCF=CFCHF—,
CH$_3$CF=CFCF$_2$—,
CH$_3$CF=CFCHF—,
CF$_3$CF=CHCF —,
CF$_3$CF=CHCH$_2$—,
CHF$_2$CF=CHCHF—,
CH$_2$FCF=CHCF$_2$—,
CH$_2$FCF=CHCH$_2$—,
CH$_3$CF=CHCHF—,
CF$_3$CH=CFCF$_2$—,
CF$_3$CH=CFCH$_2$—,
CHF$_2$CH=CFCHF—,
CH$_2$FCH=CFCF$_2$—,
CH$_2$FCH=CFCH$_2$—,
CH$_3$CH=CFCHF—,
CF$_3$CH=CHCF$_2$—,
CF$_3$CH=CHCH$_2$—,
CHF$_2$CH=CHCHF—,
CH$_2$FCH=CHCF$_2$—,
CH$_2$FCH=CHCH$_2$—,
CH$_3$CH=CHCHF—, and CH$_3$CH=CHCH$_2$—.

5. The compound of claim 1 wherein said R' is selected from the group consisting of CF$_3$CF$_2$CF=CF—,
CF$_3$CF=CFCH$_2$—,
CHF$_2$CF=CFCHF—,
CH$_2$FCF=CFCF$_2$—,
CH$_2$FCF=CFCH$_2$—,
CH$_3$CF=CFCHF—,
CF$_3$CF=CFCH$_2$—,
CF$_3$CF=CHCHF—,
CHF$_2$CF=CHCF$_2$—,
CHF$_2$CF=CHCH$_2$—,
CH$_2$FCF=CHCHF—,
CH$_3$CF=CHCF$_2$—,
CH$_3$CF=CHCH$_2$—,
CF$_3$CH=CFCHF—,
CHF$_2$CH=CFCF$_2$—,
CHF$_2$CH=CFCH$_2$—,
CH$_3$CH=CFCF$_2$—,
CH$_3$CH=CFCH$_2$—,
CF$_3$CH=CHCHF—,
CHF$_2$CH=CHCF$_2$—,
CHF$_2$CH=CHCH$_2$—,
CH$_2$FCH=CHCHF—,
CH$_3$CH=CHCF$_2$—, CF$_3$CHFCF=CF—,
CHF$_2$CF$_2$CF=CF—,
CHF$_2$CH$_2$=CF—,
CH$_2$FCHFCF=CF—,
CH$_3$CF$_2$CF=CF—,
CH$_3$CH$_2$CF=CF—,
CF$_3$CHFCF=CH—,
CHF$_2$CF$_2$CF=CH—,
CHF$_2$CH$_2$CF=CH—,
CH$_2$FCHFCF=CH—,
CH$_3$CF$_2$CF=CH—,
CH$_3$CH$_2$CF=CH—,
CF$_3$CHFCH=CF—,
CHF$_2$CF$_2$CH=CF—,
CHF$_2$CH$_2$CH=CF—,
CH$_2$FCHFCH=CF—,
CH$_3$CF$_2$CH=CF—,
CH$_3$CH$_2$CH=CF—,
CF$_3$CHFCH=CH—,
CHF$_2$CF$_2$CH=CH—,
CH$_2$FCH$_2$CH=CH—,
CH$_3$CHFCH=CH—, and CH$_3$CH$_2$CH=CH—.

CF$_3$CH$_2$CF=CF—,
CHF$_2$CHFCF=CF—,
CH$_2$FF$_2$CF=CF—,
CH$_2$FCH$_2$CF=CF—,
CH$_3$CHFCF=CF—,
CF$_3$CF$_2$CF=CH—,
CF$_3$CH$_2$CF=CH—,
CHF$_2$CHFCF=CH—,
CH$_2$FF$_2$CF=CH—,
CH$_2$FCH$_2$CF=CH—,
CH$_3$CHFCF=CH—,
CF$_3$CF$_2$CH=CF—,
CF$_3$CH$_2$CH=CF—,
CHF$_2$CHFCH=CF—,
CH$_2$FF$_2$CH=CF—,
CH$_2$FCH$_2$CH=CF—,
CH$_3$CHFCH=CF—,
CF$_3$CF$_2$CH=CH—,
CF$_3$CH$_2$CH=CH—,
CH$_2$FCHFCH=CH—,
CH$_3$CF$_2$CH=CH—,

6. The compound of claim 2 wherein each of said R is the same.

7. The compound of claim 3 wherein each of said R is the same.

8. The compound of claim 4 wherein each of said R is the same.

9. The compound of claim 5 wherein each of said R is the same.

10. The compound of claim 2 wherein each of said R is CF$_3$.

11. The compound of claim 3 wherein each of said R is CF$_3$.

12. The compound of claim 4 wherein each of said R is CF$_3$.

13. The compound of claim 5 wherein each of said R is CF$_3$.

14. The compound of claim 1 selected from the group consisting of 3-trifluoromethyl-1,1,2,4,4,4-hexafluoro-1-butene; 3-trifluoromethyl-1,1,4,4,4-pentafluoro-1-butene; 3-trifluoromethyl-1,4,4,4-tetrafluoro-1-butene; 3-trifluoromethyl-2,4,4,4-tetrafluoro-1-butene; 4-trifluoromethyl-1,1,2,3,3,5,5,5-octafluoro-1-pentene; 4-trifluoromethyl-1,1,1,2,3,5,5,5-octafluoro-2-pentene; 4-trifluoromethyl-2,3,3,5,5,5-hexafluoro-1-pentene; 4-trifluoromethyl-2,3,5,5,5-pentafluoro-1-pentene; 4-trifluoromethyl-3,3,5,5,5-pentafluoro-1-pentene; and 4-trifluoromethyl-3,5,5,5-tetrafluoro-1-pentene.

* * * * *

UNITED STATES PATENT AND TRADEMARK OFFICE
CERTIFICATE OF CORRECTION

PATENT NO. : 5,087,777

DATED : February 11, 1992

INVENTOR(S) : Chien C. Li, Kane D. Cook and Rajat S. Basu

It is certified that error appears in the above-identified patent and that said Letters Patent is hereby corrected as shown below:

Col 24, line 48, Replace Claim 2 with attached.

Col 24, line 62, Replace Claim 3 with attached.

Col 25, line 24, Replace Claim 4 with attached.

Col 25, line 50, Replace Claim 5 with attached.

Signed and Sealed this

Twenty-first Day of December, 1993

Attest:

BRUCE LEHMAN

Attesting Officer

Commissioner of Patents and Trademarks

2. The compound of claim 1 wherein said R' is selected from the group consisting of $CF_2=CF-$, $CF_2=CH-$, $CF_2=CFCF_2-$, $CF_2=CFCH_2-$, $CF_2=CFCHF-$, $CF_2=CHCF_2-$, $CF_2=CHCH_2-$, $CF_2=CHCHF-$, $CF_3CF=CF-$, $CF_3CF=CH-$, $CF_3CH=CF-$, $CF_3CH=CH-$, $CHF=CF-$, $CHF=CH-$, $CHF=CFCF_2-$, $CHF=CFCH_2-$, $CHF=CFCHF-$, $CHF=CHCF_2-$, $CHF=CHCH_2-$, $CHF=CHCHF-$, $CHF_2CF=CF-$, $CHF_2CF=CH-$, $CHF_2CH=CF-$, $CHF_2CH=CH-$, $CH_2=CF-$, $CH_2=CH-$, $CH_2=CFCF_2-$, $CH_2=CFCH_2-$, $CH_2=CFCHF-$, $CH_2=CHCF_2-$, $CH_2=CHCH_2-$, $CH_2=CHCHF-$, $CH_2FCF=CF-$, $CH_2FCF=CH-$, $CH_2FCH=CF-$, and $CH_2FCH=CH-CF_3$.

3. The compound of claim 1 wherein said R' is selected from the group consisting of $CH_3CF=CF-$, $CH_3CF=CH-$, $CH_3CH=CF-$, $CH_3CH=CH-$, $CF_2=CFCF_2CF_2-$, $CF_2=CFCF_2CHF-$, $CF_2=CFCF_2CH_2-$, $CF_2=CFCHFCF_2-$, $CF_2=CFCHFCHF-$, $CF_2=CFCHFCH_2-$, $CF_2=CFCH_2CF_2-$, $CF_2=CFCH_2CHF-$, $CF_2=CFCH_2CH_2-$, $CF_2=CHCF_2CF_2-$, $CF_2=CHCF_2CHF-$, $CF_2=CHCF_2CH_2-$, $CF_2=CHCHFCF_2-$, $CF_2=CHCHFCHF-$, $CF_2=CHCHFCH_2-$, $CF_2=CHCH_2CF_2-$, $CF_2=CHCH_2CHF-$, $CF_2=CHCH_2CH_2-$, $CHF=CFCF_2CF_2-$, $CHF=CFCF_2CHF-$, $CHF=CFCF_2CH_2-$, $CHF=CFCHFCF_2-$, $CHF=CFCHFCHF-$, $CHF=CFCHFCH_2-$, $CHF=CFCH_2CF_2-$, $CHF=CFCH_2CHF-$, $CHF=CFCH_2CH_2-$, $CHF=CHCF_2CF_2-$, $CHF=CHCF_2CHF-$, $CHF=CHCF_2CH_2-$, $CHF=CHCHFCF_2-$, $CHF=CHCHFCHF-$, $CHF=CHCHFCH_2-$, $CHF=CHCH_2CF_2-$, $CHF=CHCH_2CHF-$, $CHF=CHCH_2CH_2-$, $CH_2=CFCF_2CF_2-$, $CH_2=CFCF_2CHF-$, $CH_2=CFCF_2CH_2-$, $CH_2=CFCHFCF_2-$, $CH_2=CFCHFCHF-$, $CH_2=CFCHFCH_2-$, $CH_2=CFCH_2CF_2-$, $CH_2=CFCH_2CHF-$, $CH_2=CFCH_2CH_2-$, $CH_2=CHCF_2CF_2-$, $CH_2=CHCF_2CHF-$, $CH_2=CHCF_2CH_2-$, $CH_2=CHCHFCF_2-$, $CH_2=CHCHFCHF-$, $CH_2=CHCHFCH_2-$, $CH_2=CHCH_2CF_2-$, $CH_2=CHCH_2CHF-$, and $CH_2=CHCH_2CH_2-$.

4. The compound of claim 1 wherein said R' is selected from the group consisting of $CF_3CF=CFCF_2-$, $CF_3CF=CFCHF-$, $CF_3CF=CFCH_2-$, $CHF_2CF=CFCF_2-$, $CHF_2CF=CFCHF-$, $CHF_2CF=CFCH_2-$, $CH_2FCF=CFCF_2-$, $CH_2FCF=CFCHF-$, $CH_2FCF=CFCH_2-$, $CH_3CF=CFCF_2-$, $CH_3CF=CFCHF-$, $CH_3CF=CFCH_2-$, $CF_3CF=CHCF_2-$, $CF_3CF=CHCHF-$, $CF_3CF=CHCH_2-$, $CHF_2CF=CHCF_2-$, $CHF_2CF=CHCHF-$, $CHF_2CF=CHCH_2-$, $CH_2FCF=CHCF_2-$, $CH_2FCF=CHCHF-$, $CH_2FCF=CHCH_2-$, $CH_3CF=CHCF_2-$, $CH_3CF=CHCHF-$, $CH_3CF=CHCH_2-$, $CF_3CH=CFCF_2-$, $CF_3CH=CFCHF-$, $CF_3CH=CFCH_2-$, $CHF_2CH=CFCF_2-$, $CHF_2CH=CFCHF-$, $CHF_2CH=CFCH_2-$, $CH_2FCH=CFCF_2-$, $CH_2FCH=CFCHF-$, $CH_2FCH=CFCH_2-$, $CH_3CH=CFCF_2-$, $CH_3CH=CFCHF-$, $CH_3CH=CFCH_2-$, $CF_3CH=CHCF_2-$, $CF_3CH=CHCHF-$, $CF_3CH=CHCH_2-$, $CHF_2CH=CHCF_2-$, $CHF_2CH=CHCHF-$, $CHF_2CH=CHCH_2-$, $CH_2FCH=CHCF_2-$, $CH_2FCH=CHCHF-$, $CH_2FCH=CHCH_2-$, $CH_3CH=CHCF_2-$, $CH_3CH=CHCHF-$, and $CH_3CH=CHCH_2-$.

5. The compound of claim 1 wherein said R' is selected from the group consisting of $CF_3CF_2CF=CF-$, $CF_3CHFCF=CF-$, $CF_3CH_2CF=CF-$, $CHF_2CF_2CF=CF-$, $CHF_2CHFCF=CF-$, $CHF_2CH_2CF=CF-$, $CH_2FF_2CF=CF-$, $CH_2FCHFCF=CF-$, $CH_2FCH_2CF=CF-$, $CH_3CF_2CF=CF-$, $CH_3CHFCF=CF-$, $CH_3CH_2CF=CF-$, $CF_3CF_2CF=CH-$, $CF_3CHFCF=CH-$, $CF_3CH_2CF=CH-$, $CHF_2CF_2CF=CH-$, $CHF_2CHFCF=CH-$, $CHF_2CH_2CF=CH-$, $CH_2FF_2CF=CH-$, $CH_2FCHFCF=CH-$, $CH_2FCH_2CF=CH-$, $CH_3CF_2CF=CH-$, $CH_3CHFCF=CH-$, $CH_3CH_2CF=CH-$, $CF_3CF_2CH=CF-$, $CF_3CHFCH=CF-$, $CF_3CH_2CH=CF-$, $CHF_2CF_2CH=CF-$, $CHF_2CHFCH=CF-$, $CHF_2CH_2CH=CF-$, $CH_2FF_2CH=CF-$, $CH_2FCHFCH=CF-$, $CH_2FCH_2CH=CF-$, $CH_3CF_2CH=CF-$, $CH_3CHFCH=CF-$, $CH_3CH_2CH=CF-$, $CF_3CF_2CH=CH-$, $CF_3CHFCH=CH-$, $CF_3CH_2CH=CH-$, $CHF_2CF_2CH=CH-$, $CHF_2CHFCH=CH-$, $CHF_2CH_2CH=CH-$, $CH_2FF_2CH=CH-$, $CH_2FCHFCH=CH-$, $CH_2FCH_2CH=CH-$, $CH_3CF_2CH=CH-$, $CH_3CHFCH=CH-$, and $CH_3CH_2CH=CH-$.